United States Patent
Bates

(10) Patent No.: US 10,861,604 B2
(45) Date of Patent: Dec. 8, 2020

(54) SYSTEMS AND METHODS FOR AUTOMATED MEDICAL DIAGNOSTICS

(71) Applicant: James Stewart Bates, Paradise Valley, AZ (US)

(72) Inventor: James Stewart Bates, Paradise Valley, AZ (US)

(73) Assignee: AdviNow, Inc., Paradise Valley, AZ (US)

( * ) Notice: Subject to any disclaimer, the term of this patent is extended or adjusted under 35 U.S.C. 154(b) by 450 days.

(21) Appl. No.: 15/344,390

(22) Filed: Nov. 4, 2016

(65) Prior Publication Data

US 2017/0323064 A1 Nov. 9, 2017

Related U.S. Application Data

(60) Provisional application No. 62/332,422, filed on May 5, 2016.

(51) Int. Cl.
*G16H 50/20* (2018.01)
*G06F 19/00* (2018.01)

(52) U.S. Cl.
CPC .................. *G16H 50/20* (2018.01)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS 5,617,857 A * 4/1997 Chader ................... A61B 5/06
128/899
6,915,254 B1 7/2005 Heinze et al.
(Continued)

FOREIGN PATENT DOCUMENTS

EP 1027459 A1 8/2000
EP 1316039 6/2003
(Continued)

OTHER PUBLICATIONS

International Search Report dated Aug. 23, 2018, in international Patent Application No. PCT/US18/37163, filed Jun. 12, 2018 (2 pgs).

(Continued)

*Primary Examiner* — Robert W Morgan
*Assistant Examiner* — Charles P Coleman
(74) *Attorney, Agent, or Firm* — North Weber and Baugh LLP; Michael North

(57) ABSTRACT

Presented are systems and methods that provide patients with diagnostic measurement tools and clear and concise audio/video guidance to reliably and accurately perform clinical grade diagnostic measurements of key vital signs. In various embodiments, this is accomplished by using an automated remote (or local, e.g., in the form of a kiosk) end-to-end medical diagnostic system that monitors equipment usage for accuracy. The diagnostic system analyzes patient responses, measurement data, and patient-related information to generate diagnostic and/or treatment information that may be shared with healthcare professionals and specialists, as needed. Automation provides for timely, hassle-free, and cost-effective health care management that takes the stress out of doctor visits, while delivering personalized health care. The high accuracy of generated diagnostic data improves health care to patients and reduces the risk of medical malpractice for treating physicians.

15 Claims, 13 Drawing Sheets

(58) Field of Classification Search
CPC ........ G16H 20/17; G16H 30/00; G16H 40/00;
G16H 50/00; G16H 70/00; G16H 80/00;
G16H 50/20; G06F 19/325
USPC .................................................. 705/2, 3, 20
See application file for complete search history.

(56) References Cited

U.S. PATENT DOCUMENTS

| | | | |
|---|---|---|---|
| 6,970,742 | B2 | 11/2005 | Mann et al. |
| 7,171,311 | B2 | 1/2007 | Dai et al. |
| 7,197,492 | B2 | 3/2007 | Sullivan |
| 7,384,146 | B2 | 6/2008 | Covannon et al. |
| 7,627,489 | B2 | 12/2009 | Schaeffer et al. |
| 8,043,224 | B2 | 10/2011 | Sarel |
| 8,140,154 | B2 * | 3/2012 | Donnelly ............ A61B 5/02055 607/6 |
| 8,275,442 | B2 | 9/2012 | Allison |
| 8,358,822 | B2 | 1/2013 | Sun et al. |
| 8,463,346 | B2 | 6/2013 | Kuhn et al. |
| 8,548,828 | B1 | 10/2013 | Longmire |
| 9,460,400 | B2 | 10/2016 | De Bruin et al. |
| 9,552,745 | B1 | 1/2017 | Gutierrez Morales |
| 10,143,373 | B2 | 12/2018 | Gilad-Gilor |
| 10,339,719 | B2 * | 7/2019 | Jagga .................... A61B 6/037 |
| 2001/0021801 | A1 | 9/2001 | Bardy |
| 2001/0029322 | A1 | 10/2001 | Iliff |
| 2002/0065457 | A1 * | 5/2002 | Kuth ...................... A61B 6/00 600/407 |
| 2003/0028406 | A1 | 2/2003 | Herz et al. |
| 2005/0054938 | A1 | 3/2005 | Wehman et al. |
| 2005/0075907 | A1 | 4/2005 | Rao |
| 2005/0165285 | A1 | 7/2005 | Iliff |
| 2005/0251030 | A1 | 11/2005 | Azar et al. |
| 2006/0036619 | A1 * | 2/2006 | Fuerst .................... G06Q 10/10 |
| 2006/0173712 | A1 | 8/2006 | Joubert |
| 2006/0271400 | A1 | 11/2006 | Clements et al. |
| 2007/0104316 | A1 | 5/2007 | Ruchala et al. |
| 2007/0168233 | A1 | 7/2007 | Hymel |
| 2007/0244702 | A1 | 10/2007 | Kahn et al. |
| 2007/0265542 | A1 | 11/2007 | Bardy |
| 2008/0071578 | A1 | 3/2008 | Herz et al. |
| 2008/0081973 | A1 | 4/2008 | Hoarau |
| 2008/0183030 | A1 | 7/2008 | Shiri et al. |
| 2008/0228528 | A1 | 9/2008 | Keen et al. |
| 2008/0275738 | A1 | 11/2008 | Shillingburg |
| 2009/0062623 | A1 | 3/2009 | Cohen et al. |
| 2009/0062670 | A1 | 3/2009 | Sterling et al. |
| 2009/0187425 | A1 | 7/2009 | Thompson |
| 2009/0240524 | A1 | 9/2009 | Bluth |
| 2009/0299766 | A1 * | 12/2009 | Friedlander ............ G06Q 10/00 705/3 |
| 2010/0023351 | A1 | 1/2010 | Lifshits et al. |
| 2010/0057651 | A1 | 3/2010 | Fung et al. |
| 2010/0280350 | A1 | 11/2010 | Zhang |
| 2010/0298899 | A1 * | 11/2010 | Donnelly ............ A61B 5/02055 607/6 |
| 2011/0053128 | A1 | 3/2011 | Alman |
| 2011/0087135 | A1 | 4/2011 | Ferzli et al. |
| 2011/0112793 | A1 | 5/2011 | Diebold et al. |
| 2011/0166465 | A1 | 7/2011 | Clements et al. |
| 2011/0202370 | A1 | 8/2011 | Green, III et al. |
| 2011/0295621 | A1 * | 12/2011 | Farooq .................... G06Q 10/10 705/3 |
| 2012/0022348 | A1 | 1/2012 | Droitcour et al. |
| 2012/0065987 | A1 * | 3/2012 | Farooq .................... G06F 19/328 705/2 |
| 2012/0078062 | A1 | 3/2012 | Bagchi et al. |
| 2012/0084092 | A1 * | 4/2012 | Kozuch .................. G06Q 50/22 705/2 |
| 2012/0191476 | A1 | 7/2012 | Reid et al. |
| 2012/0232930 | A1 | 9/2012 | Schmidt et al. |
| 2012/0247472 | A1 | 10/2012 | Lynch, Jr. |
| 2012/0289825 | A1 | 11/2012 | Rai et al. |
| 2013/0226601 | A1 | 8/2013 | Razmi et al. |
| 2013/0268203 | A1 | 10/2013 | Pyloth |
| 2013/0289362 | A1 * | 10/2013 | Kruglick ............... A61B 5/0059 600/301 |
| 2013/0297217 | A1 | 11/2013 | Bangera et al. |
| 2013/0297348 | A1 | 11/2013 | Cardoza et al. |
| 2013/0338447 | A1 | 12/2013 | Gilad-Gilor |
| 2014/0052463 | A1 | 2/2014 | Cashman et al. |
| 2014/0058755 | A1 | 2/2014 | Macoviak et al. |
| 2014/0074454 | A1 | 3/2014 | Brown et al. |
| 2014/0095201 | A1 * | 4/2014 | Farooq .................... G16H 50/30 705/3 |
| 2014/0100885 | A1 | 4/2014 | Stern |
| 2014/0236630 | A1 | 8/2014 | Murata |
| 2014/0244278 | A1 | 8/2014 | Park et al. |
| 2014/0275928 | A1 | 8/2014 | Acquista et al. |
| 2014/0257047 | A1 | 9/2014 | Sillay et al. |
| 2014/0257852 | A1 | 9/2014 | Walker et al. |
| 2014/0266787 | A1 | 9/2014 | Tran |
| 2014/0275849 | A1 | 9/2014 | Acquista |
| 2014/0276552 | A1 | 9/2014 | Nguyen, Jr. et al. |
| 2014/0279746 | A1 | 9/2014 | De Bruin et al. |
| 2014/0303680 | A1 | 10/2014 | Donnelly et al. |
| 2014/0324453 | A1 | 10/2014 | Herz et al. |
| 2014/0359722 | A1 | 12/2014 | Schultz et al. |
| 2015/0031964 | A1 | 1/2015 | Bly et al. |
| 2015/0087926 | A1 | 3/2015 | Raz et al. |
| 2015/0213194 | A1 | 7/2015 | Wolf et al. |
| 2015/0227620 | A1 | 8/2015 | Takeuchi et al. |
| 2015/0238107 | A1 | 8/2015 | Acquista et al. |
| 2015/0244687 | A1 | 8/2015 | Perez et al. |
| 2015/0248536 | A1 | 9/2015 | Tawil et al. |
| 2015/0347385 | A1 | 12/2015 | Flor et al. |
| 2016/0000515 | A1 | 1/2016 | Sels et al. |
| 2016/0023046 | A1 | 1/2016 | Evin et al. |
| 2016/0038092 | A1 | 2/2016 | Golay |
| 2016/0098542 | A1 | 4/2016 | Costantini et al. |
| 2016/0140318 | A1 | 5/2016 | Stangel |
| 2016/0267222 | A1 | 9/2016 | Larcom et al. |
| 2016/0302710 | A1 | 10/2016 | Alberts et al. |
| 2016/0342753 | A1 | 11/2016 | Feazell |
| 2017/0011172 | A1 | 1/2017 | Rauchel |
| 2017/0039502 | A1 | 2/2017 | Guman et al. |
| 2017/0076501 | A1 * | 3/2017 | Jagga .................... G16H 40/63 |
| 2017/0079580 | A1 | 3/2017 | Moore et al. |
| 2017/0105650 | A1 | 4/2017 | Peacock, III et al. |
| 2017/0154212 | A1 | 6/2017 | Feris et al. |
| 2017/0169171 | A1 * | 6/2017 | Loeb .................... G06F 19/328 |
| 2017/0199987 | A1 * | 7/2017 | Loeb .................... G06F 19/328 |
| 2017/0262614 | A1 | 9/2017 | Vishnubhatla et al. |
| 2017/0311843 | A1 * | 11/2017 | Bailey .................... A61B 34/20 |
| 2017/0323064 | A1 | 11/2017 | Bates |
| 2017/0323071 | A1 | 11/2017 | Bates |
| 2017/0344711 | A1 | 11/2017 | Liu et al. |
| 2018/0025121 | A1 | 1/2018 | Fei et al. |
| 2018/0121857 | A1 | 5/2018 | Gutman et al. |
| 2018/0140223 | A1 * | 5/2018 | Kheradpir ............ A61B 34/20 |
| 2018/0192965 | A1 | 7/2018 | Rose et al. |
| 2018/0286135 | A1 * | 10/2018 | Jagga .................... G16H 40/63 |
| 2018/0330058 | A1 | 11/2018 | Bates |
| 2018/0330059 | A1 | 11/2018 | Bates et al. |
| 2019/0080161 | A1 * | 3/2019 | Vilsmeier .......... G06K 9/00369 |
| 2019/0095957 | A1 | 3/2019 | Ibarria et al. |
| 2019/0139648 | A1 | 5/2019 | Rutledge et al. |
| 2019/0180873 | A1 | 6/2019 | Kartoun et al. |

FOREIGN PATENT DOCUMENTS

| | | |
|---|---|---|
| TW | 201629895 A | 8/2016 |
| WO | 9904043 A1 | 1/1999 |
| WO | 02001470 A1 | 3/2002 |
| WO | 2014088933 A1 | 6/2014 |
| WO | 2016178973 A1 | 11/2016 |
| WO | 2017192918 A1 | 11/2017 |

OTHER PUBLICATIONS

Written Opinion dated Aug. 23, 2018, in international Patent Application No. PCT/US18/37163, filed Jun. 12, 2018 (9 pgs).

(56) References Cited

OTHER PUBLICATIONS

International Search Report dated Jul. 26, 2017, in International Patent Application No. PCT/US2017/031158, filed May 4, 2017 (5 pgs).
Written Opinion dated Jul. 26, 2017, in International Patent Application No. PCT/US2017/031158, filed May 4, 2017 (5 pgs).
International Search Report dated Jul. 20, 2017, in International Patent Application No. PCT/US2017/031159, filed May 4, 2017 (6 pgs).
Written Opinion dated Jul. 20, 2017, in International Patent Application No. PCT/US2017/031159, filed May 4, 2017 (9 pgs).
International Search Report dated Aug. 1, 2017, in International Patent Application No. PCT/US2017/031163, filed May 4, 2017 (6 pgs).
Written Opinion dated Aug. 1, 2017, in International Patent Application No. PCT/US2017/031163, filed May 4, 2017 (7 pgs).
Response to Final Office Action dated Nov. 5, 2019, in related U.S. Appl. No. 15/590,721, (14 pgs).
Non-Final Office Action dated Oct. 29, 2019, in related U.S. Appl. No. 15/863,078, (74 pgs).
Non-Final Office Action dated Feb. 21, 2019, in U.S. Appl. No. 15/352,488 (31 pgs).
Response to Non-Final Office Action filed Feb. 26, 2019, in Application No. 15/352,488 (17 pgs).
International Search Report and Written Opinion dated Apr. 15, 2019 in International Patent Application No. PCT/US19/12166, filed Jan. 3, 2019 (14 pgs).
International Search Report and Written Opinion dated Apr. 11, 2019 in International Patent Application No. PCT/US19/12901, filed Jan. 9, 2019 (7 pgs).
Non-Final Office Action dated Dec. 26, 2018, in U.S. Appl. No. 15/628,411, (12 pgs).
Non-Final Office Action Response filed May 8, 2019, in U.S. Appl. No. 15/628,411, (8 pgs).
Non-Final Office Action dated May 14, 2019, in U.S. Appl. No. 15/590,997, (42 pgs).
Non-Final Office Action dated May 15, 2019, in U.S. Appl. No. 15/590,721, (48 pgs).
International Search Report and Written Opinion dated May 13, 2019, in International Application No. PCT/US2019/020848, filed Mar. 5, 2019 (8 pgs).
International Search Report and Written Opinion dated May 17, 2019, in International Application No. PCT/US2019/020844, filed Mar. 5, 2019 (14 pgs).
Final Office Action Response and RCE filed Aug. 20, 2019, in related U.S. Appl. No. 15/352,488, (17 pgs).
Non-Final Office Action Response filed Oct. 17, 2019, in related U.S. Appl. No. 15/355,472, (12 pgs).
Non-Final Office Action Response filed Oct. 17, 2019, in related U.S. Appl. No. 15/371,000, (9 pgs).
Advisory Action dated Aug. 12, 2019, in related U.S. Appl. No. 15/628,411, (3 pgs).
Advisory Action Response and RCE filed Sep. 9, 2019, in related U.S. Appl. No. 15/628,411, (8 pgs).
Final Office Action dated Sep. 16, 2019, in related U.S. Appl. No. 15/590,997, (55 pgs).
Non-Final Office Action dated Sep. 23, 2019, in related U.S. Appl. No. 16/170,775, (39 pgs).
Final Office Action dated Oct. 8, 2019, in related U.S. Appl. No. 15/590,721, (67 pgs).
Non-Final Office Action Response filed Jun. 4, 2019, in U.S. Appl. No. 15/590,997, (13 pgs).
Non-Final Office Action Response filed Jul. 30, 2019, in U.S. Appl. No. 15/590,721, (16 pgs).
International Search Report and Written Opinion dated Jun. 14, 2019, in International Application No. PCT/US2019/020845, filed Mar. 5, 2019 (7 pgs).
Final Office Action dated Jun. 20, 2019, in U.S. Appl. No. 15/352,488, (24 pgs).
Final Office Action dated Jun. 20, 2019, in U.S. Appl. No. 15/628,411, (36 pgs).
Final Office Action Response filed Jul. 30, 2019, in U.S. Appl. No. 15/628,411, (10 pgs).
Video available from the Internet at <URL: https://www.azbio.tv/video/1173cba2664c41078b757f11f2d5073b>, "AdviNow Medical—2018 Fast Lane Honoree", by AZBio, published on Oct. 6, 2018. (1 pg).
Non-Final Office Action dated Jul. 17, 2019, in U.S. Appl. No. 15/355,472, (43 pgs).
Non-Final Office Action dated Jul. 17, 2019, in U.S. Appl. No. 15/371,000, (37 pgs).
Response to Final Office Action filed Nov. 15, 2019, in related application No. 115/590,997, (12 pgs).
Response to Non-Final Office Action filed Nov. 21, 2019, in related U.S. Appl. No. 16/170,775, (14 pgs).
Non-Final Office Action dated Jan. 6, 2020, in related U.S. Appl. No. 15/628,411, (32 pgs).
Supplementary Search Report dated Nov. 27, 2019, in related European application No. EP 17 79 3393, (15 pgs).
Advisory Action dated Nov. 29, 2019, in related U.S. Appl. No. 15/590,721, (3 pgs).
Response to Final Office Action and RCE filed on Jan. 16, 2020, in related U.S. Appl. No. 15/590,721, (15 pgs).
Advisory Action dated Dec. 5, 2019, in related U.S. Appl. No. 15/590,997, (3 pgs).
Response to Final Office Action and RCE filed on Jan. 16, 2020, in related U.S. Appl. No. 15/590,997, (12 pgs).
Non-Final Office Action dated Jan. 30, 2020, in related U.S. Appl. No. 15/352,488, (13 pgs).
Final Office Action dated Jan. 31, 2020, in related U.S. Appl. No. 15/355,472, (19 pgs).
Final Office Action dated Jan. 30, 2020, in related U.S. Appl. No. 15/371,000, (17 pgs).
Applicant-Initiated Interview Summary dated Jan. 31, 2020, in related U.S. Appl. No. 15/863,078, (8 pgs).
Applicant-Initiated Interview Summary dated Nov. 18, 2019, in related U.S. Appl. No. 15/352,488, (3 pgs).
International Search Report and Written Opinion dated Jul. 27, 2018, in International Patent Application No. PCT/US2018/030989, filed May 3, 2018 (6 pgs).
International Search Report and Written Opinion dated Jul. 27, 2018, in International Patent Application No. PCT/US2018/30991, filed May 3, 2018 (6 pgs).

* cited by examiner

Heart rate sensor,
Otoscope,
Digital stethoscope,
In-Ear thermometer,
Blood ox sensor,
Hi-Definition camera,
Spirometry,
Blood pressure,
Glucometer,
Ultrasound,
EKG/ECG,
Body fluid sample collectors,
Eye slit lamp
Weight scale,
BMI,
Body fat percentage,
Body water,
Muscle mass Remote Auto-Diagnostic Kit 1200

FIG. 12

SYSTEMS AND METHODS FOR AUTOMATED MEDICAL DIAGNOSTICS

CROSS REFERENCE TO RELATED PATENT APPLICATIONS

The present application claims priority benefit, under 35 U.S.C. § 119(e), to and commonly-assigned U.S. Patent Application No. 62/332,422, filed on May 5, 2016, entitled "AUTOMATED MEDICAL DIAGNOSTIC SYSTEM," listing as inventor James Stewart Bates, which application is herein incorporated by reference as to its entire content. Each reference mentioned in this patent document is incorporated by reference herein in its entirety.

BACKGROUND

A. Technical Field

The present disclosure relates to medical consulting, and more particularly, to systems and methods for automated medical diagnostics.

B. Background of the Invention

Patients' common problems with scheduling an appointment with a primary doctor when needed or in a time-efficient manner is causing a gradual shift away from a patient establishing and relying on a life-long relationship with a single general practitioner, who diagnoses and treats the patient in health-related matters, towards patients opting to receive readily available treatment in urgent care facilities that are located near home, work, or school and provide relatively easy access to healthcare without the inconvenience of appointments that oftentimes must be scheduled weeks or months ahead of time. Yet, the decreasing importance of primary doctors makes it difficult for different treating physicians to maintain a reasonably complete medical record for each patient, which results in a patient having to repeat a great amount of information each time when visiting a different facility or different doctor. In some cases, patients confronted with lengthy and time-consuming patient questionnaires fail to provide accurate information important for a proper medical treatment, whether for the sake of expediting their visit or other reasons. In addition, studies have shown that patients attending urgent care or emergency facilities may in fact worsen their health conditions due to the risk of exposure to viruses or bacteria in medical facilities despite the medical profession's efforts to minimize the number of such instances.

Through consistent regulation changes, electronic health record changes and pressure from the payers, health care facilities and providers are looking for ways to make patient intake, triage, diagnosis, treatment, electronic health record data entry, treatment, billing, and patient follow-up activity more efficient to provide better patient experience and increase the doctor to patient throughput per hour, while simultaneously reducing cost.

The desire to increase access to health care providers, a pressing need to reduce health care costs in developed countries and the goal of making health care available to a larger population in less developed countries have fueled the idea of telemedicine. In most cases, however, video or audio conferencing with a doctor does not provide sufficient patient-physician interaction that is necessary to allow for a proper medical diagnosis to efficiently serve patients.

What is a need are systems and methods that ensure reliable remote or local medical patient intake, triage, diagnosis, treatment, electronic health record data entry/management, treatment, billing and patient follow-up activity so that physicians may allocate patient time more efficiently and, in other instances, allow individuals to manage their own health, thereby, reducing health care costs.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 12 shows exemplary list of devices in an exemplary remote auto-diagnostic medical kit according to embodiments of the present disclosure.

DETAILED DESCRIPTION OF THE PREFERRED EMBODIMENTS

Figure 1:
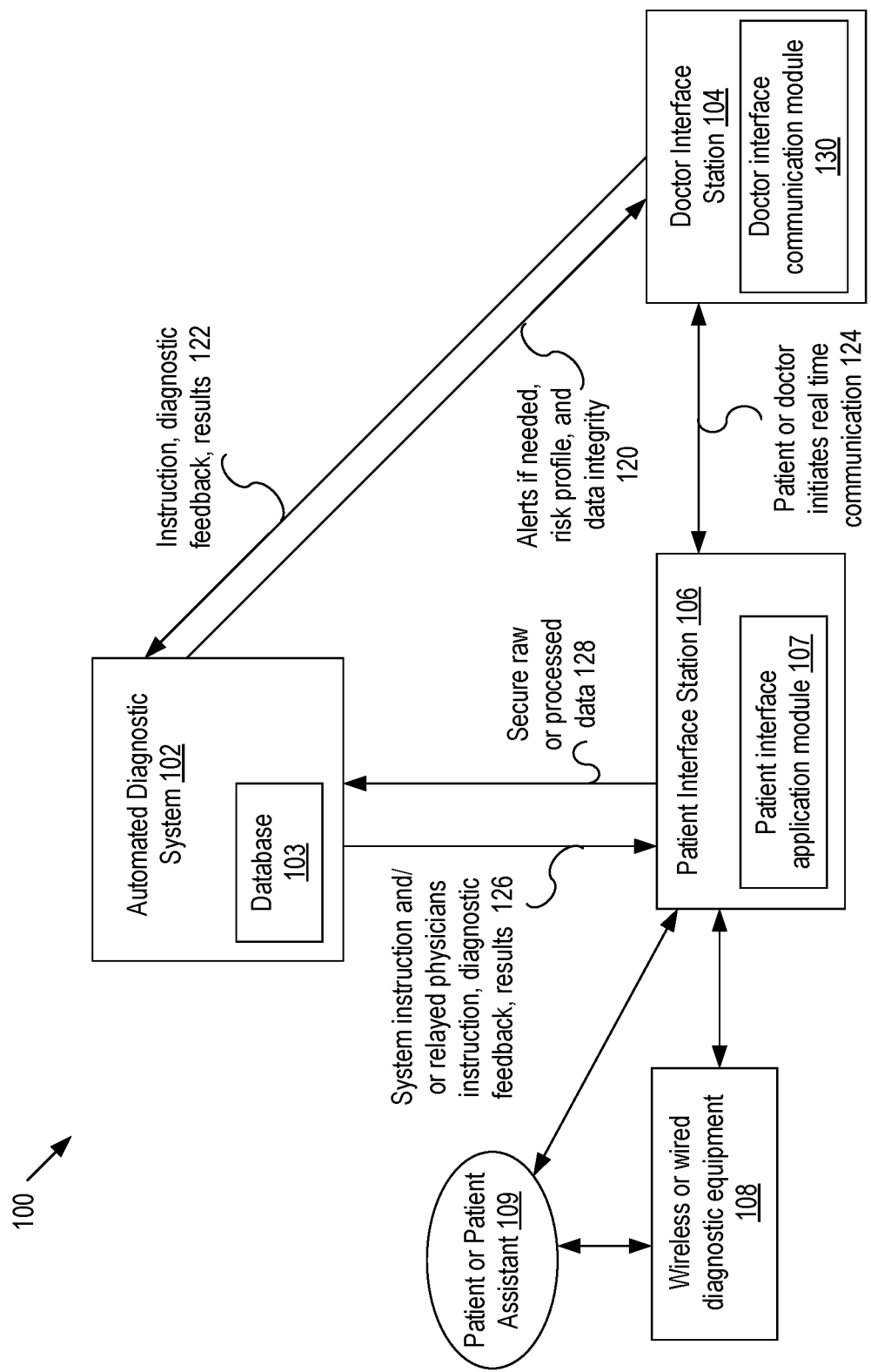
FIG. 1 shows a schematic diagram of a diagnostic system according to embodiments of the present disclosure.

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, a device, or a method on a tangible computer-readable medium.

Elements/components shown in diagrams are illustrative of exemplary embodiments of the disclosure and are meant to avoid obscuring the disclosure. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components/elements. Components/elements may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms "coupled" "connected" or "communicatively coupled" shall be understood to include direct connections, indirect connections through one or more intermediary devices, and wireless connections.

Furthermore, one skilled in the art shall recognize that: (1) certain steps may optionally be performed; (2) steps may not be limited to the specific order set forth herein; and (3) certain steps may be performed in different orders; and (4) certain steps may be done concurrently.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims.

Furthermore, the use of certain terms in various places in the specification is for illustration and should not be construed as limiting. A service, function, or resource is not limited to a single service, function, or resource; usage of these terms may refer to a grouping of related services, functions, or resources, which may be distributed or aggregated.

In this document, the term "doctor" refers to any physician, healthcare provider, or person directed by a physician. "Patient" is a person being examined or anyone assisting such person. The term illness may be used interchangeably with the term diagnosis. As used herein, "answer" or "question" refers to one or more of 1) an answer to a question, 2) a measurement or measurement request (e.g., a measurement performed by a "patient"), and 3) a symptom (e.g., a symptom selected by a "patient").

FIG. 1 shows a schematic diagram of a diagnostic system according to embodiments of the present disclosure. Diagnostic system 100 comprises automated diagnostic system 102, patient interface station 106, doctor interface station 104, and diagnostic equipment 108. Both patient interface station 106 and doctor interface station 104 may be implemented into any tablet, computer, mobile device, or other electronic device. Diagnostic equipment 108 is designed to collect mainly diagnostic patient data and may comprise one or more diagnostic devices, e.g., in a home diagnostic medical kit, that generates diagnostic data based on physical and non-physical characteristics of a patient. An exemplary list of diagnostic devices is shown in FIG. 12 comprising heart rate sensor, otoscope, digital stethoscope, in-ear thermometer, blood oxygen sensor, high-definition camera, spirometry, blood pressure meter, glucometer, ultrasound, EKG/ECG meter, body fluid sample collectors, eye slit lamp, weight scale, and any other device known in the art that may aid in performing a medical diagnosis.

In operation, the patient 109 may enter patient-related data, such as health history, patient characteristics, symptoms, health concerns, vital signs data, images, and sound patterns into patient interface station 106. The patient 109 may use any means of communication, such as voice control, to enter data, e.g., in the form of a questionnaire, into patient interface station 106. Patient interface station 106 may provide raw or processed patient-related data via a secure communication to automated diagnostic system 102.

In embodiments, the patient 109 may log into a software application to fill out a questionnaire that may help to diagnose one or more medical conditions. For example, the patient 109 may be prompted by a software application that provides guidance by describing, in any desired level of detail, how to use diagnostic equipment 108 to administer a diagnostic test or how to make diagnostic measurements (e.g., how to take temperature) for any device that may be part of diagnostic equipment 108 to enable measurements of clinical grade accuracy.

In embodiments, the patient 109 may use diagnostic equipment 108 as a vital signs monitoring system to create a patient health profile that may serve as a baseline for subsequent measurements. Patient-related data may be securely stored in database 103 or a secure remote server (not shown) coupled to automated diagnostic system 102. In embodiments, automated diagnostic system 102 enables interaction between a patient 109 and remotely located medical personnel, such that a patient may receive instructions from a healthcare professional, for example, by communicating via a software application. A doctor may log into a cloud-based system (not shown) to access patient-related data via doctor interface station 104. In embodiments, automated diagnostic system 102 presents automated diagnostic suggestions to a doctor, who may verify or modify the suggested information.

In embodiments, based on a one more patient questionnaires, data gathered by diagnostic equipment 108, patient feedback, and historic diagnostic information, one or more of instructions, feedback, other relevant information, and results 122 may be provided to the patient 109. In embodiments, sequence of instructions, feedback, and/or results 122 may be adjusted based on medical database decision vectors. In embodiments, devices 108 generate diagnostic data in response to patient answers and/or measurements of a patient's vital signs using the decision vectors to generate a diagnostic result.

In embodiments, diagnostic equipment 108 comprises a number of sensors, such as an accelerometer, a gyroscope, a pressure sensor, a camera, an altimeter, an IR LED, and a proximity sensor that may be coupled to one or more medical devices, e.g., a thermometer, to perform diagnostic measurements and/or monitor a patient's use of diagnostic equipment 108 for accuracy. The camera, in addition to taking pictures of the patient, may use image or facial recognition software to aid a patient in locating suitable positions for taking a measurement on the patient's body.

Facial recognition may serve to identify eyes, mouth, nose, ears, torso, or any other part of the patients as a reference. One skilled in the art will appreciate that not all sensors need to operate at all times. Any number of sensors may be partially or completely disabled, e.g., to save energy. Each sensor may be associated with a device usage accuracy score.

Examples of diagnostic data that diagnostic equipment 108 may generate comprise body temperature, blood pressure, images, sound, heart rate, blood oxygen level, motion, ultrasound, pressure or gas analysis, continuous positive airway pressure (CPAP), electrocardiogram (EKG), electroencephalogram (EEG), Electrocardiography (ECG), BMI, muscle mass, blood, urine, and any other patient-related data 128. In embodiments, patient-related data 128 may be derived from a wearable or implantable monitoring device that may gather sample data.

In embodiments, an IR LED or other identifiable marker (not shown) may be affixed to diagnostic equipment 108, e.g., a temperature sensor or stethoscope, to track the position and placement of diagnostic equipment 108. In embodiments, a camera detects the light emitted by the IR LED or other markers in the picture and may be used as an identifiable marker to aid the camera to determine the position of diagnostic equipment 108.

In embodiments, machine vision software may be used to track and overlay or superimpose, e.g., on a screen, the position of the IR LED with the desired target location at which the patient should place diagnostic equipment 108, thereby, aiding the patient to properly place or align a sensor and ensure accurate and reliable readings. Once diagnostic equipment 108, e.g., a stethoscope is at a desired target location on a patient's torso, the patient may be prompted by optical or visual cues to breath according to instructions or do other actions to facilitate medical measurements and to start the measurement.

In embodiments, one or more sensors that may be attached to diagnostic equipment 108 monitor the placement and usage of diagnostic equipment 108 by periodically or continuously recording data and comparing measured data, such as location, movement, and angles, to an expected data model and/or an error threshold to ensure measurement accuracy. A patient may be instructed to adjust an angle, location, or motion of diagnostic equipment 108, e.g., to adjust its state to avoid low-accuracy or faulty measurement readings. Sensor data may be compared, for example, against an idealized patient device measurement data or ideal device measurement data as would be expected from diagnostic equipment 108. Feedback from diagnostic equipment 108 (e.g., sensors and camera) and actual measurement data may be used to instruct the patient to properly align diagnostic equipment 108 during a measurement. Each sensor type or movement around the measurement may be used to create a device usage accuracy score for use in a medical diagnosis algorithm. The actual device measurement data may also be used to create a measurement accuracy score for use by the medical diagnostic algorithm.

In embodiments, the machine vision software may use an overlay method to mimic a patient's movements by using detailed interactive instructions, e.g., a character, an image of the patient, a graphic or an avatar, that is displayed on a monitor in order to provide real-time feedback to the patient. The instructions, image, or avatar may start or stop and decide what help instruction to display based on the type of device and information from the camera and sensors, e.g., image, position, location, angle or orientation, of diagnostic equipment 108 compared to an ideal sensor output and/or location in relation to the measured location on the patient's body. This further aids the patient in correctly positioning operating diagnostic equipment 108 relative to the patient's body, ensures a high level of accuracy when operating diagnostic equipment 108, and solves potential issues that the patient may encounter.

In embodiments, once automated diagnostic system 102 detects unexpected data, e.g., data representing an unwanted movement, location, measurement data, etc., a validation process comprising a calculation of a trustworthiness score or reliability factor in order to gauge measurement accuracy is initiated, such that if the accuracy of the measured data falls below a desired level, the patient 109 may be asked to either repeat a measurement or request assistance by a live assistant, who may answer questions, e.g., remotely via an application, and help with correct equipment usage or alert a nearby assistant to help with the use of diagnostic equipment 108. In addition to instructing the patient to repeat a measurement and answer additional questions, the validation process may comprise calculating a trustworthiness score based on the measured or re-measured data.

In embodiments, upon request 124 automated diagnostic system 102 enables a patient-doctor interaction by granting the patient and a doctor access to diagnostic system 100. The patient may enter data, take measurements, and submit images and audio files or any other information to the application or web portal. The doctor may enter access that information, for example, to review a diagnosis generated by automated diagnostic system 102, and generate, confirm, or modify instructions for the patient. Patient-doctor interaction while not required for diagnostic and treatment, if used, may occur in person, real-time via an audio/video application, or by any other means of communication.

In embodiments, automated diagnostic system 102 may utilize images generated from a diagnostic examination of mouth, throat, eyes, ears, skin, extremities, surface abnormalities, internal imaging sources, and other suitable image data, and/or audio data generated from diagnostic examination of heart, lungs, abdomen, chest, joint motion, voice, and any other audio data sources. Automated diagnostic system 102 may also utilize patient lab tests, medical images, or any other medical data.

In embodiments, automated diagnostic system 102 enables a medical examination of patient 109, for example, using patient medical devices, e.g., ultrasound, to detect sprains, contusions, or fractures, and automatically provide diagnostic recommendations regarding the patient's condition. In embodiments, diagnosis comprises medical database decision vectors that are based, at least partially, on the patient's self or assistant measured vitals, the accuracy score of each measurement, the sensor medical device usage accuracy score, the regional illness trends, and other information used in generally accepted medical knowledge evaluations steps. The decision vectors and associated algorithm, which may be installed in automated diagnostic system 102, may utilize one or more-dimensional data, patient history, patient questionnaire feedback, and pattern recognition or pattern matching for classification using images and audio data. The medical device usage accuracy score generator may be implemented within automated diagnostic system 102 and may utilize an error vector of each sensor to create a device usage accuracy score and the actual patient measured device data to create a measurement data accuracy score.

Figure 6:
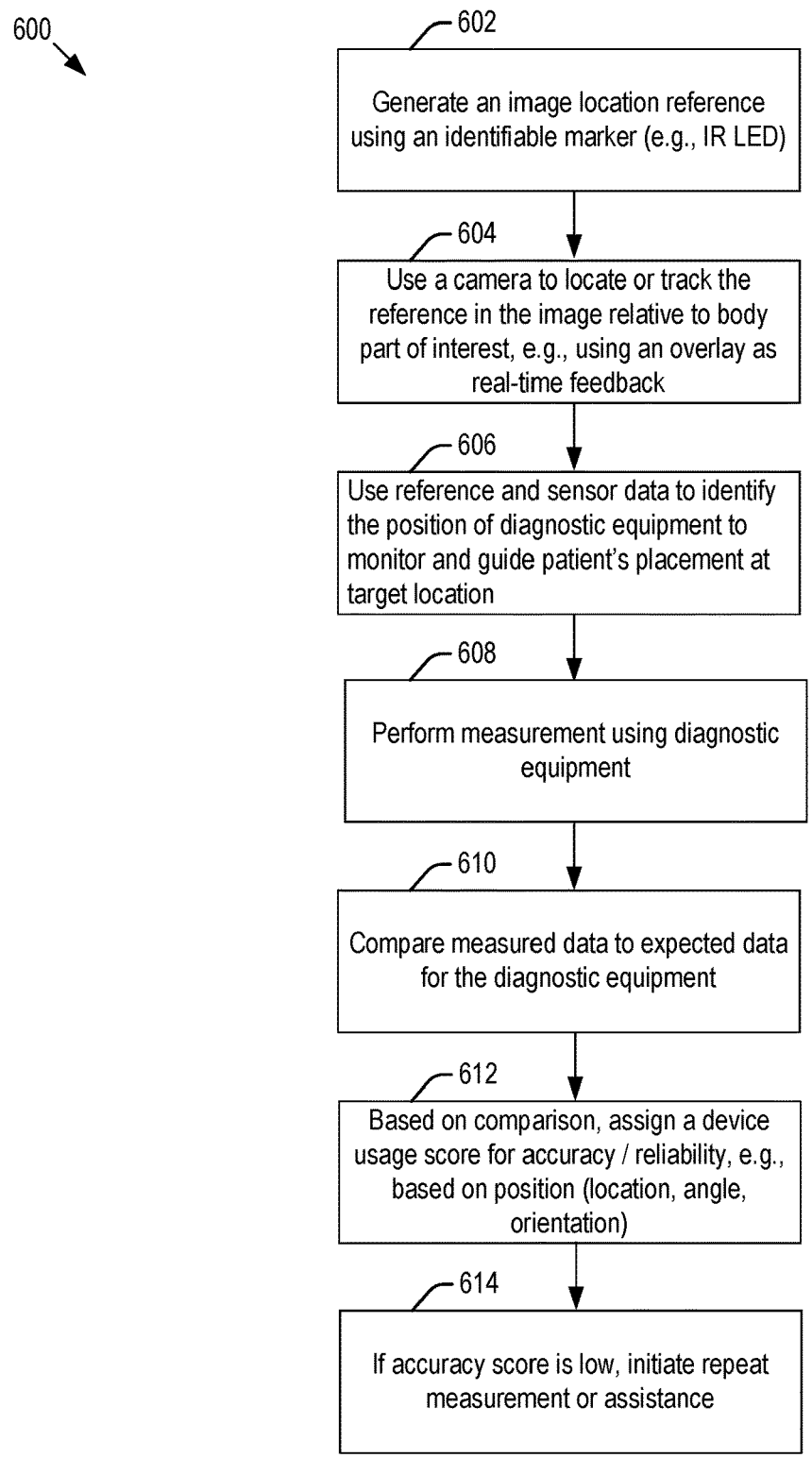
FIG. 6 illustrates a process for increasing measurement accuracy according to embodiments of the present disclosure.

FIG. 6 illustrates a process for increasing measurement accuracy according to embodiments of the present disclosure. Process 600 starts at step 602 when, for example, in response to a motion detector sensing an acceleration, an identifiable marker (e.g., IR LED signal) is used to generate, e.g., within an image, a reference having one or more characteristics that are different from other parts of the image.

At step 604, a receiver, an image, or video device, e.g., a camera, is used to locate or track the reference, e.g., within an image, relative to a body part of a patient. In embodiments, an overlay method may be used to overlay the patient image against an ideal model of device usage to enable real-time feedback to the patient.

At step 606, the reference along with other sensor data may be used to identify a position, location, angle, orientation, or usage, associated with a diagnostic device to monitor and guide a patient's placement of the diagnostic device at target location.

At step 608, measurements using the diagnostic equipment may be performed. In embodiments, the measured data, e.g., stethoscope readings, mouth, ears, nose, skin pictures, and other data associated with a physical condition is automatically recorded and usage accuracy of the diagnostic equipment is tracked. The system may analyze each clinical measured image data and compare traits from a database that detect an incomplete image for each target body part to track accuracy of measurement and provide a score. If the score is below a certain threshold, the system will give detailed guidance in taking a correct image, i.e., change angle or depth of an otoscope in nose/ear and mouth to receive a complete image. It is noted that if a device (e.g., IR LED) is used as identifiable marker, the device may be deactivated at times to conserve energy.

At step 610, in embodiments, one or more sensors associated with the diagnostic equipment monitor movement of the diagnostic equipment relative to the patient and compare movement data to an ideal model or expected data.

At step 612, based on the comparison, an accuracy or reliability score for usage of the diagnostic equipment may be assigned to the measurement data and/or the diagnostic equipment.

At step 614, if the accuracy score is low, a repeat measurement/assistance is requested.

In embodiments, one or more illness specific (irritated inner ear, irregular heart beat audio, etc.) markers may be identified in measured image or audio data, e.g., by applying filters and algorithms to an audio or video file. The identified markers may then be compared with identifiable markers in a diagnostic database that may comprise image/audio files comprising identifiable markers associated with expected measurement data. Based on the comparison a medical condition, such as an irregular heartbeat or irritated inner ear, may be determined allowing for a medical diagnosis. In embodiments, the comparison utilizes one of an audio, image, and video pattern matching algorithm. Based on the comparison, images, audio, or video comprising the markers may be provided to a doctor to assist in comparing images and, ultimately, performing a medical diagnosis, e.g., to verify an inner ear illness, such as an infected inner ear.

Returning to FIG. 1 In embodiments, automated diagnostic system 102 may output diagnosis and/or treatment information that is communicated to the patient 109, for example, by electronically communicating to the patient or through a medical professional either electronically or in person a treatment guideline that may include a prescription for medication. In embodiments, prescriptions may be communicated directly to a pharmacy for pick-up or automated home delivery.

In embodiments, automated diagnostic system 102 may generate an overall risk profile of the patient 109 and recommend steps to reduce the risk of overlooking potentially dangerous conditions or guide the patient 109 to a nearby facility that can treat a potentially dangerous condition. The risk profile may assist a treating doctor in fulfilling duties to the patient, for example, to carefully review and evaluate the patient and, if deemed necessary, refer the patient to a specialist, initiate further testing, etc. This reduces the potential for negligence and, thus, medical malpractice lawsuits.

Figure 8:
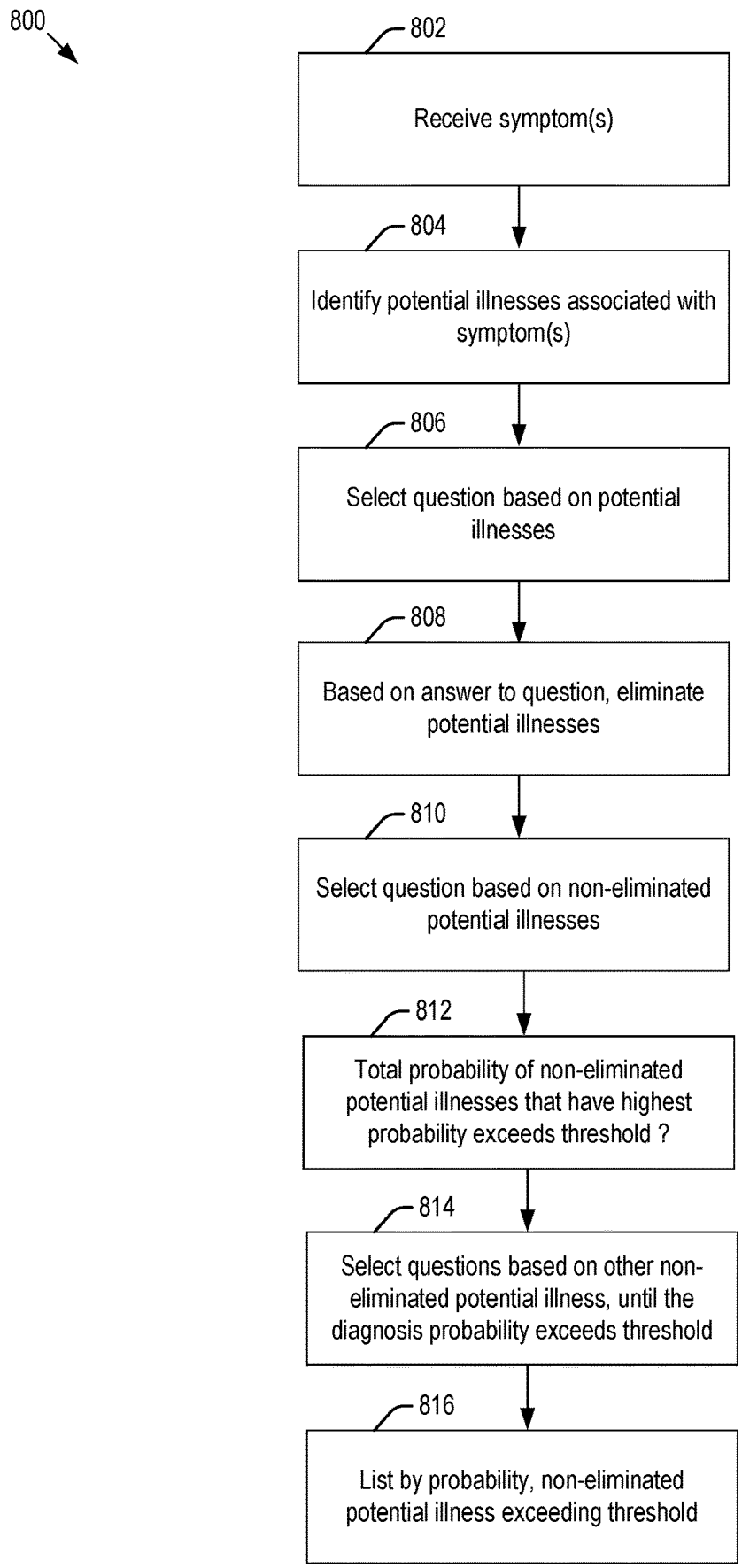
FIG. 8 illustrates a process for generating a diagnosis probability according to embodiments of the present disclosure.

FIG. 8 illustrates a process for generating a diagnosis probability according to embodiments of the present disclosure. In embodiments, machine learning may be applied to patient-provided and other data to improve the data weights used in the algorithm to eliminate a relatively large number of potential illnesses and narrow the list of potential illnesses. For example, by using a self-learning and medical database decision vectors combined with an algorithm, after a relatively low number of iterations of patient answers and measurements, a diagnosis that has a likelihood greater than a certain percentage, e.g., 50%, may be generated.

In embodiments, reducing the number of questions to a set of questions that may identify a particular illness comprises selecting answers based on symptom, illness, measurements or patient history data weights. A data weight may be used by the algorithm by comparing or matching, for example, the patient's input that may be compared to data in the database that are related to the particular illness. Based on the match a probability of the illness reflecting an accurate diagnosis may be calculated.

In detail, in embodiments, based on the patient's answers, such as self-identified zones of pain or problem zones or conditions, the patient is provided with a number of questions or symptoms or request for medical device measurements that relate to that problem zone. The patient may be prompted to identify a first symptom (e.g., headache) from the set of symptoms and, based on keywords in the patient's response that match keywords in a database, a set of questions and measurement requests may be generated to identify additional symptoms (e.g., fever). In embodiments, a question or measurement regarding a second symptom may be selected based on a highest weighted symptom related to the first symptom, such that, for example, based on medical database decision vectors, as many diagnoses as possible may be eliminated from a probability matrix.

In embodiments, an elimination process may be repeated until a relatively small number of potential illnesses (e.g., five illnesses), each having been assigned a relatively high diagnosis probability (e.g., 90%), is identified. Then, in embodiments, subsequent illness-specific questions or measurements are selected to further increase the statistical weight (i.e., the probability) of one of the identified illnesses to an even higher level prior to determining that the selected illness is a correct diagnosis.

In embodiments, the database comprises illnesses and weighted data values for each illness. Weightings may represent the likelihood that a patient having a particular illness would demonstrate the characteristic, symptom, history, description, measurement or other information.

In embodiments, initial data weight may be entered into the database and confirmed by healthcare professionals. In embodiments, initial weightings are updated by the self-learning decision tool. In other words, over time, individual weights are adjusted based on actual patient usage of diagnostic system 102 and doctor selection of illnesses and treatments. The weightings may also be adjusted using historical patient records. This learning process may be used to optimize the predictive value for each diagnosis. In embodiments, the initial weights are chosen such that each illness is associated with a uniqueness coefficient, e.g., by a predetermined amount, from that of another illness. The diagnostic database weightings and relationships and algorithm may be continuously updated by medical professionals to account for new research or illness information for location-based outbreaks or other items.

In embodiments, diagnosis probabilities are calculated according to weightings across different datasets and weightings of, e.g., key words, history, measurement data, or patient descriptions. Each illness may be assigned a match vector that may be calculated according to results of patient interactions. Using machine learning, weightings may be adjusted, for a set of circumstances, based on any number of factors such as, e.g., the number of doctors diagnosing a certain illness; the number of patients diagnosed with that illness; and variabilities for each illness/doctor. In embodiments, based on adjusted weight factors, medical database decision vectors may be generated, adjusted, and used to generate a diagnosis probability that allows to predict a diagnosis for a particular illness with higher probability and within a relatively small number of steps.

In embodiments, when two or more potential illness are identified, questions about, e.g., symptoms, may be tailored to identify which of the two or more potential illness exist. In embodiments, tailored questions are asked until the likelihood of further questions would not increase the likelihood of that illness by more than a certain percentage (e.g., 1%). In embodiments, based on the diagnosis probabilities, a list of potential illness is ranked by probability and output. In embodiments, if a final probability is less than a certain threshold (e.g., 90%), additional testing, e.g., lab testing, may be initiated or suggested.

In embodiments, each measured data entry is tied to a trustworthiness score for patient measurement data and each patient interaction with the system will carry an answer trustworthiness score (as not all question may be answered truthfully), both discussed above with respect to FIG. 1, and are adjusted lower, for example, when contradictory patient answers are detected and a follow-up question with slightly different wording is asked.

In embodiments, if, based on the symptoms/questions asked, two illnesses have the same likelihood, one of the illnesses is randomly selected to ask further questions or measurements that determine whether the selected illness is the correct one. If the further questions or measurements or other tests do not increase the likelihood/match, the other illness is selected to ask additional questions or measurements or other tests. In embodiments, if more than two illness have the same probability score, the process may be repeated until an illness with the highest match is determined to present to the physician or patient for next steps. If multiple illnesses have the same probability, the results are presented to the healthcare professional as the patient potentially having more than one illness.

In embodiments, patient interactions (answers, measurements, history, etc.) are monitored over a period of time to determine whether the symptoms of the illness are in line with a previously predicted illness. Similarly, a treatment may be monitored to determine whether it results in an improvement in a patient's medical condition. In embodiments, symptoms/treatment data is used to adjust weightings, for example, weight factors in both the diagnostics and treatment decision vectors database.

FIG. 8 illustrates a process for generating a diagnosis probability according to embodiments of the present disclosure. Process 800 for generating a diagnosis probability begins at step 802 when one or more symptoms are received.

At step 804, potential illnesses associated with the symptom(s) are identified. Each potential illness may have a diagnosis probability based on each symptom, history, measurements, and other patient input or related information.

At step 806, based on the identified illnesses, a question or measurement is selected, such that the answer to the question or measurement would eliminate a large number of identified potential illnesses.

At step 808, based on an answer to the question or measurement, one or more identified illnesses, e.g., those having the lowest diagnosis probability, are eliminated.

At step 810, based on the non-eliminated illnesses, a next question is selected, again, such that the answer to the question would eliminate a relatively large number of the non-eliminated illnesses.

At step 812, it is determined whether the total probability of a number (e.g., 5) of non-eliminated illnesses having the highest probability exceeds a threshold (e.g., 80%). If not, process 800 may resume with step 808 by continuing to eliminate potential illnesses, until the probability of the non-eliminated highest probability illnesses exceeds the defined threshold.

Otherwise, at step 814, process 800 may select one of the non-eliminated illnesses, e.g., the one with the highest diagnosis probability to ask an illnesses-specific question or instruct on a measurement.

At step 816, if the answer to an illnesses-specific question or a measurement increases the diagnosis probability, further illnesses-specific questions are asked or measurements requested, until the diagnosis probability exceeds a predetermined threshold (e.g., 90%) or the increase in probability for each question falls below a certain threshold and other potential illnesses have already been considered, at which point, the specific illness may be output as the one with the highest overall diagnosis probability and listed with the other illnesses. In embodiments, non-eliminated potential illnesses whose probability exceed a threshold are output, e.g., as a list ordered by ascending probability.

In embodiments, if, at step 816, the diagnosis probability stays within a relatively small range (e.g., 5%), process 800 may select (not shown in FIG. 8) another illness, e.g., the one with the next highest diagnosis probability, for asking further illnesses-specific questions.

Figure 9:
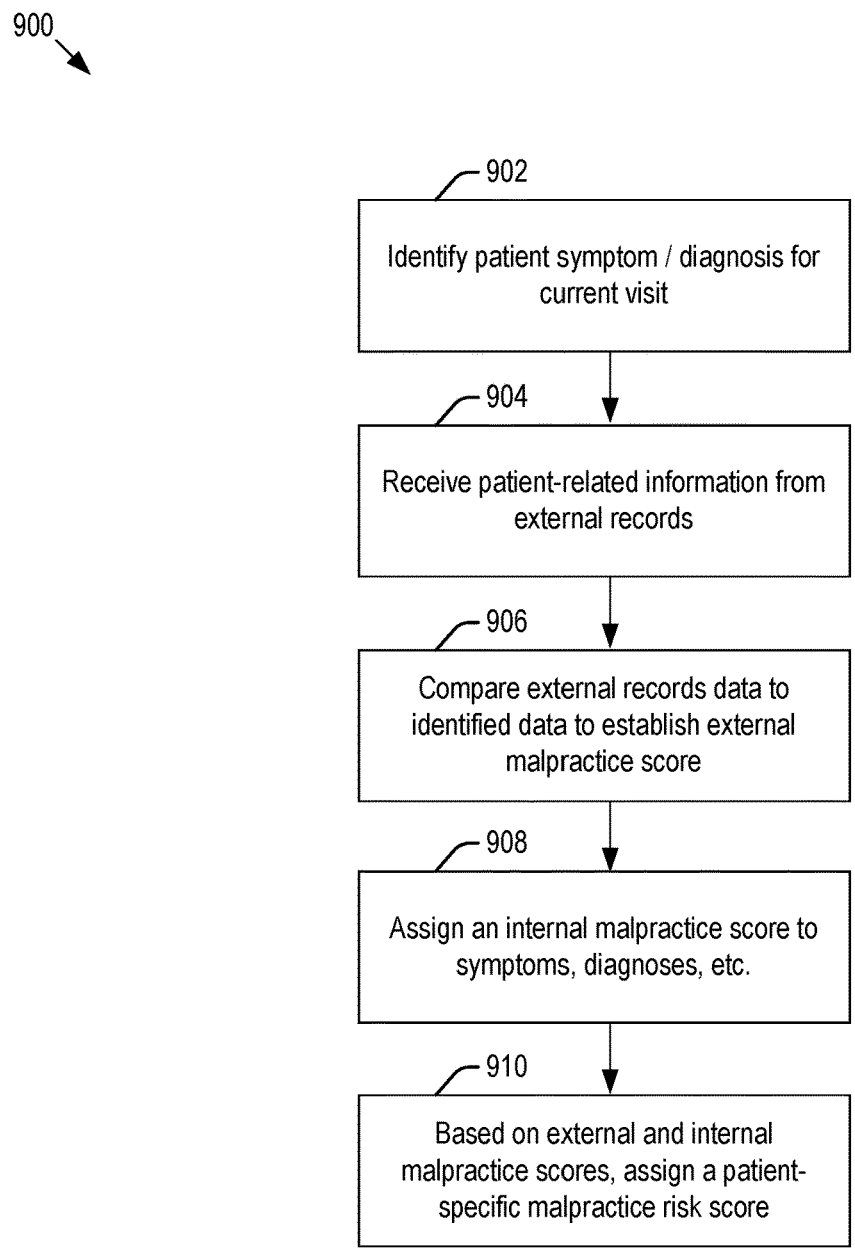
FIG. 9 is a flowchart that illustrates an exemplary process for performing a malpractice risk assessment, according to embodiments of the present disclosure.

FIG. 9 is a flowchart that illustrates an exemplary process for performing a malpractice risk assessment, according to embodiments of the present disclosure. Process 900 starts at step 902 when one or more symptoms or diagnoses of a patient are identified, e.g., for a current visit.

At step 904, patient background information related to a pending or closed malpractice lawsuit filed by or on behalf of the patient in one of more states is received, from one or more data sources, such as court and social media records (e.g., based on patient name and date of birth and other identifiable information).

At step 906, the received data is compared to detect a relationship to the identified data and a malpractice data specific score is established.

At step 908, each symptom, diagnosis, etc., may be assigned an independent internal malpractice score.

At step 910, based on the external and internal malpractice scores, a patient specific malpractice score is assigned to the patient.

It is understood that process for risk assessment need not be limited to malpractice risk assessment. Other risk factors, such as potential drug misuse or credit risk, may be used to assign a risk score to the patient.

Returning to FIG. 1, automated diagnostic system 102, in embodiments, comprises a payment feature that uses patient identification information to access a database to determine if a patient 109 has previously arranged a method of payment. If the patient database does not indicate a previously arranged method of payment, automated diagnostic system 102 may prompt the patient to enter payment information, such as insurance, bank, or credit card information. Automated diagnostic system 102 may determine whether the payment information is valid and automatically obtain an authorization from the insurance, EHR system and/or the card issuer for payment for a certain amount for services rendered by the doctor. An invoice may be electronically presented to the patient 109, e.g., upon completion of a consultation, such that the patient 109 can authorize payment of the invoice, e.g., via an electronic signature.

In embodiments, the patient database 103 (e.g., a secured cloud-based database) may comprise a security interface (not shown) that allows secure access to a patient database, for example, by using patient identification information to obtain the patient's medical history. The interface may utilize biometric, bar code, or other electronically security methods. In embodiments, diagnostic equipment 108 uses unique identifiers that are used as a control tool for measurement data. Database 103 may be a repository for any type of data created, modified, or received by diagnostic system 100, such as generated diagnostic information, information received from patient's wearable electronic devices, remote video/audio data and instructions, e.g., instructions received from a remote location or from the application.

In embodiments, fields in the patient's electronic healthcare record (EHR) (not shown in FIG. 1) are automatically populated based on one or more of questions asked by the system, measurements taken by the patient/system, diagnosis and treatment codes generated by the system, and one or more trust scores.

In addition, patient-related data documented by system 100 provide support for the level of exam the doctor performs. As in existing methods, doctors have to choose, for billing and reimbursement purposes, one of any identified codes (e.g., ICD10 currently holds approximately 97,000 medical codes) to identify an illness and provide an additional code that identifies the level of physical exam/diagnosis performed on the patient (e.g., full body physical exam) based on the illness identified by the doctor.

In embodiments, the documented questions are used to suggest to the doctor a level of exam that is supported by the illness identified so as to ensure that, e.g., the doctor does not perform unnecessary in-depth exams for minor illnesses or performs treatment that may not be covered by the patient's insurance.

In embodiments, a portion of the patient's EHR is populated based on imported patient healthcare data from one or more sources, such as an existing healthcare database. It is understood the format of imported patient healthcare data may be converted to become compatible with the EHR format of system 100. Conversely, exported patient healthcare data may be converted to be compatible, e.g., with an external EHR database.

Figure 10:
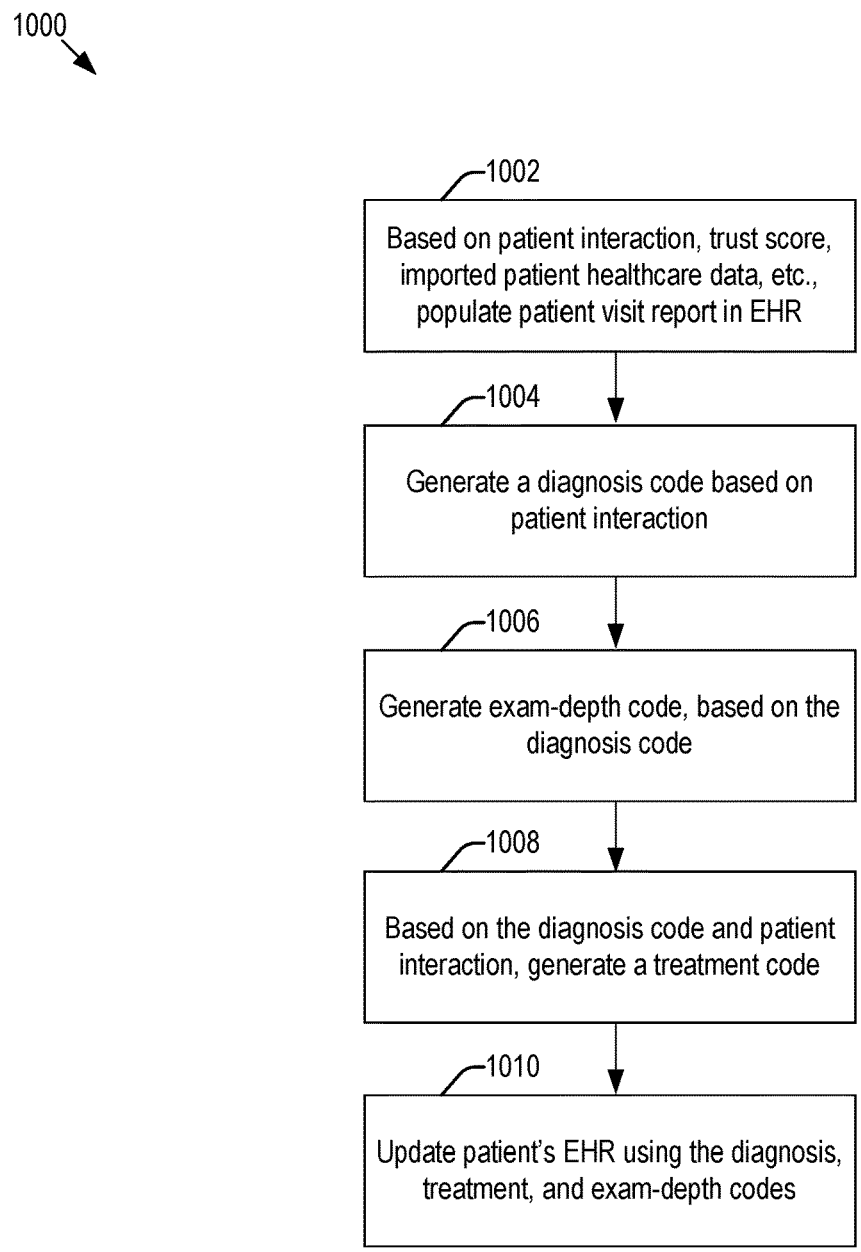
FIG. 10 is a flowchart that illustrates an exemplary process for automatically populating a patient's EHR, according to embodiments of the present disclosure.

FIG. 10 is a flowchart that illustrates an exemplary process for automatically populating a patient's EHR, according to embodiments of the present disclosure. Process 1000 starts at step 1002 when a patient visit report in the patient's EHR is populated based on one or more of, for example, a patient response, measurement data, a trust score, patient healthcare data imported from one or more external sources, such as an existing healthcare database, and a diagnosis identified by a doctor or an automated diagnostic system.

At step 1004, based on patient interaction (e.g., patient responses and measurement data), a diagnosis code, such as a standardized code, is generated that may be made available to a doctor.

At step 1006, based on the diagnosis code and patient interaction (questions asked, measurements taken, etc.), an exam-depth code is generated, for example, together with an explanation directed to a treating doctor.

At step 1008, based on the diagnose, a treatment code is generated.

At step 1010, f the patient's EHR is updated, e.g., by using the diagnosis code, the treatment code, and the exam-depth code.

It is understood that any patient-related data, such as generated trust scores and populated EHR data, may be deleted, overridden, supplemented, adjusted, or customized, for example, with additional observations and documentation related to a patient's condition. It is further understood that progress reports related to treatment may be generated at any stage of a treatment.

Returning to FIG. 1, in embodiments, upon identifying a diagnosis, system 100 generates one or more recommendations/suggestions/options for a particular treatment. In embodiments, system 100 may generate a prescription/lab test request and considers factors, such as recent research results, available drugs and possible drug interactions, the patient's medical history, traits of the patient, family history and any other factors that may affect treatment to provide treatment information for a doctor.

In embodiments, diagnosis and treatment databases are continuously updated, e.g., by health care professionals such that an optimal treatment for a particular patient, e.g., a patient identified as belonging to a certain risk group, can be administered. In embodiments, one or more treatment plans are generated that the doctor may discuss with the patient and decide on a suitable treatment. For example, one treatment plan may be tailored purely for effectiveness, another treatment plan may consider drug costs.

Figure 11:
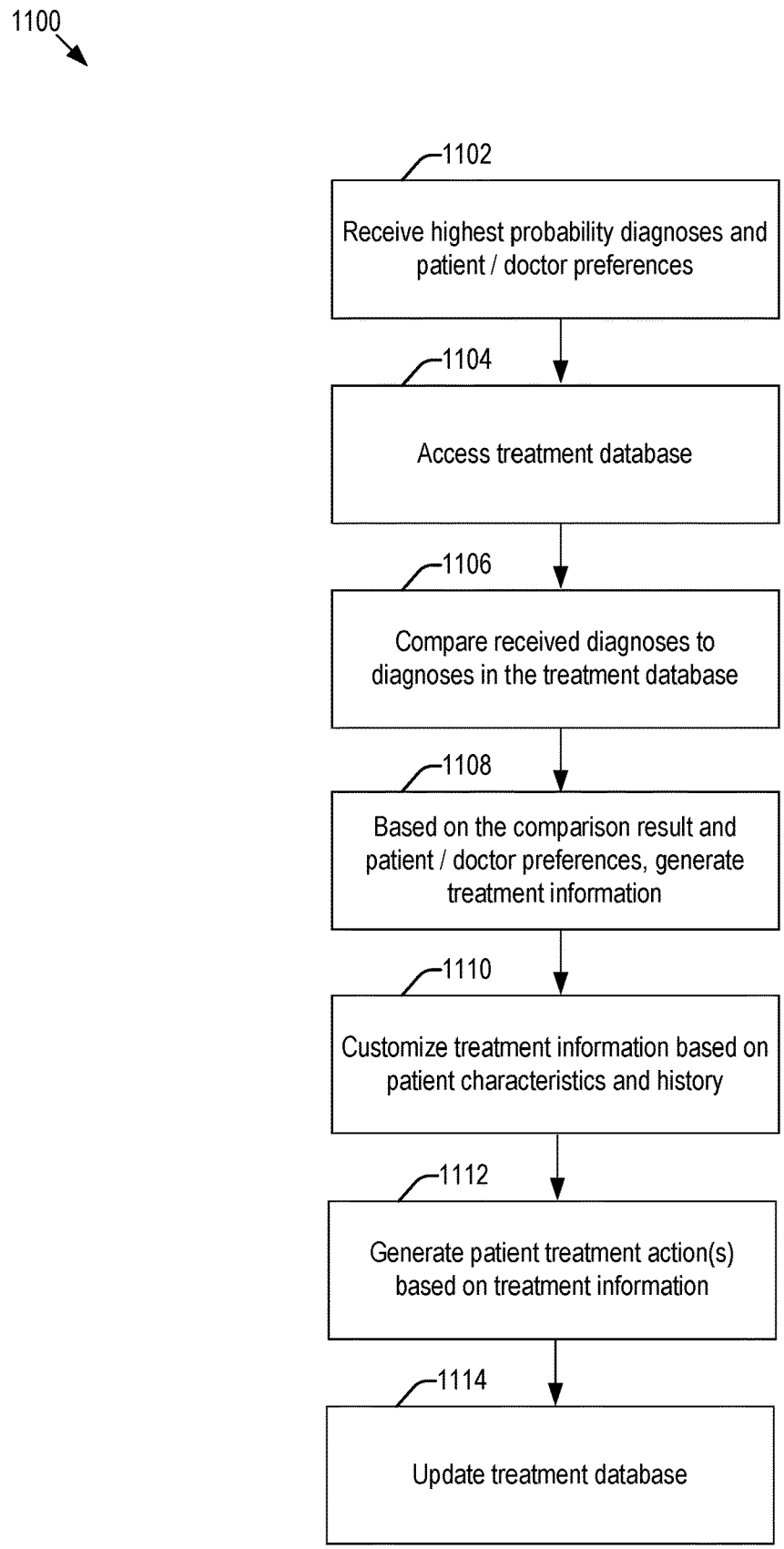
FIG. 11 illustrates an exemplary process for generating treatment information, according to embodiments of the present disclosure.

FIG. 11 illustrates an exemplary process for generating treatment information, according to embodiments of the present disclosure. Process 1100 starts at step 1102 when one or more diagnoses are received by, for example, an automated diagnostic system that considers factors, such as patient/doctor preferences, recent research results, available drugs and possible drug interactions, the patient's medical history, genetic traits of the patient, and other factors that may affect treatment.

At step 1104, a treatment database that comprises one or more diagnoses is accessed.

At step 1106, one or more of the diagnoses received at step 1102, e.g., a number of highest probability diagnoses, are compared to the one or more diagnoses in the treatment database.

At step 1108, based on the result of the comparison and, e.g., patient/doctor preferences, e.g., the cost of treatment, treatment information is generated. In embodiments, treatment information comprises at least one of a recommendation, a suggestion, and a treatment plan that is associated with one or more of the highest probability illnesses.

At step 1110, in embodiments, the treatment information is customized based on patient characteristics and history.

At step 1112, based on the treatment information, a list of patient treatment actions (e.g., prescribing a prescription) may be generated.

At step 1114, the treatment database is automatically or manually updated, e.g., by a health care professional or via a machine learning process that uses current visit patient and physician input and may use future patient visits or remote tools to track patient progress and optimize weightings.

Figure 2:
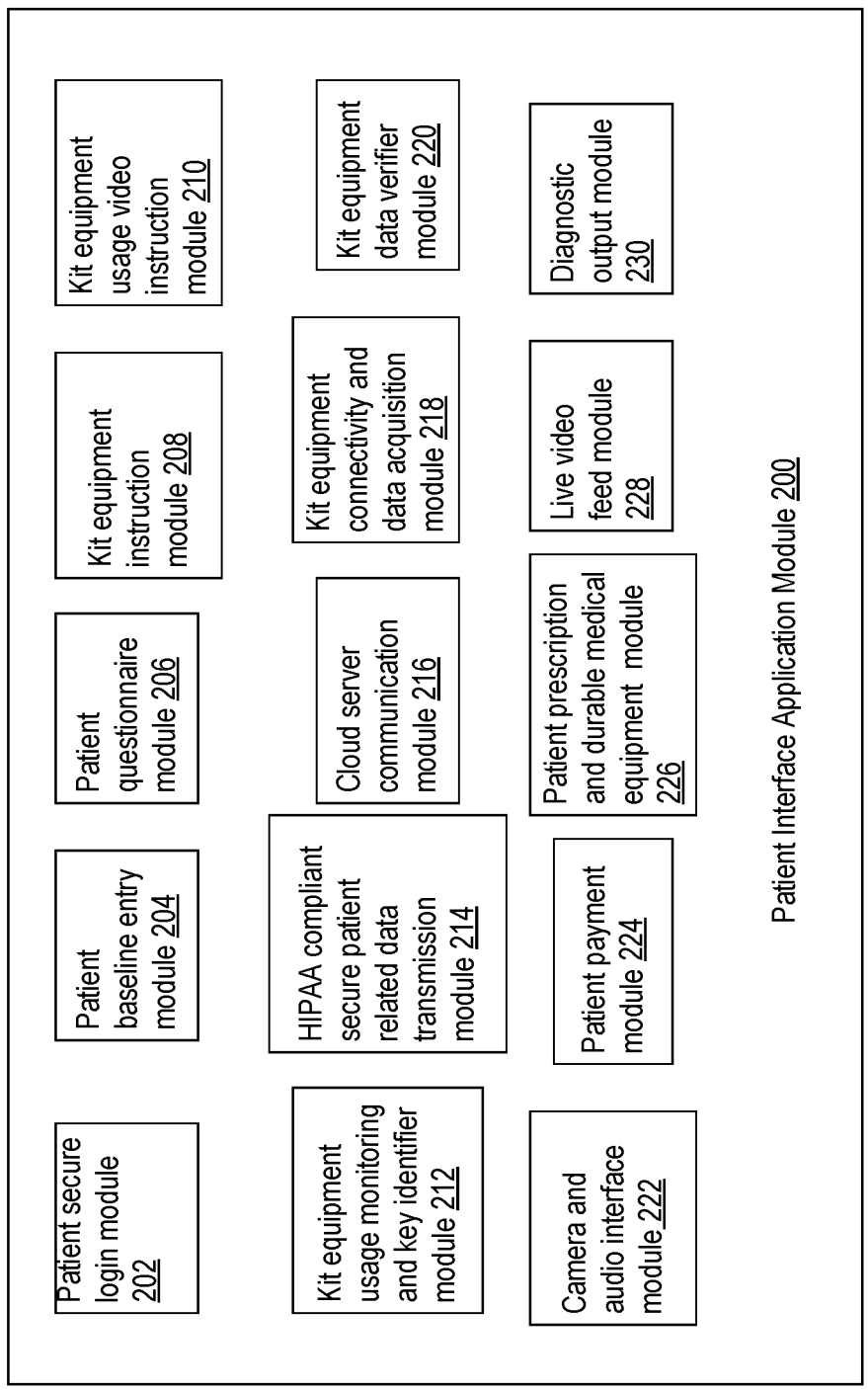
FIG. 2 shows a schematic diagram of a patient interface application module according to embodiments of the present disclosure.

FIG. 2 shows a schematic diagram of a patient interface application module according to embodiments of the present disclosure. In embodiments, each component of the patient interface application module 200 (or 107 in FIG. 1) may be implemented as software, hardware, and/or firmware. In embodiments, the patient interface application module 200 may be installed in patient interface station 106 (shown in FIG. 1) that the patient 109 has an access to. It is noted that the components 202-230 in FIG. 2 are not an exhaustive list of elements that may comprise patient interface application module 200. Also, it is noted that some of components 202-230 may be combined into one element and that one component may be implemented as multiple elements.

In embodiments, patient interface application module 200 may comprise: a patient secure login module 202 that may allow the patient to log into an automated diagnostic system (not shown in FIG. 2); patient baseline entry module 204 that may allow a patient to enter baseline data, e.g., of a relatively healthy state, into patient interface application module 200; patient questionnaire module 206 that may provide interactive questions to the patient and receive corresponding responses from the patient that the automated diagnostic system may use to diagnose a medical condition. In embodiments, performing a diagnosis comprises determining or evaluating the accuracy of data provided by the patient.

In embodiments, patient interface application module 200 comprises: a kit equipment instruction module 208 that may provide the patient with step-by-step written instructions that may guide the patient, e.g., when collecting diagnostic data of vital signs using a diagnostic kit; kit equipment usage video instruction module 210 that may provide the patient with written instruction and/or sample video, graphic, or avatar instructions on how to use devices in the diagnostic kit; kit equipment usage monitoring and key identifier module 212 that may monitor the patient's equipment usage through at least one sensor and evaluate the measured data for accuracy; HIPAA compliant secure patient related data transmission module 214 that may transmit data using a HIPAA compliant security protocol; and cloud/server communication module 216 that may control communications to a cloud system via any network protocol known in the art.

In embodiments, patient interface application module 200 may further comprise: kit equipment connectivity and data acquisition module 218 that may provide and monitor connectivity to the diagnostic kit for data acquisition; camera and audio interface module 222 that may control camera and/or audio devices that aid in taking accurate measurements; and kit equipment data verifier module 220 that may verify or authenticate data sent by the diagnostic kit.

In embodiments, patient interface application module 200 may further comprise: patient payment module 224 that may provide payment options to the patient and arrange a method of payment; patient prescription and durable medical equipment module 226 that may provide prescription and other instructions for medical equipment to the patient; live video feed module 228 that may provide various visual information to the patient; and diagnostic output module 230 that may provide diagnostic output and/or feedback of the physician to the patient. In embodiments, patient interface application module 200 comprises a treatment module (not shown in FIG. 2) that may provide treatment options from which the patient may select a treatment plan and receive detailed treatment recommendations, suggested lab tests, medical imaging procedures, etc.

Figure 3:
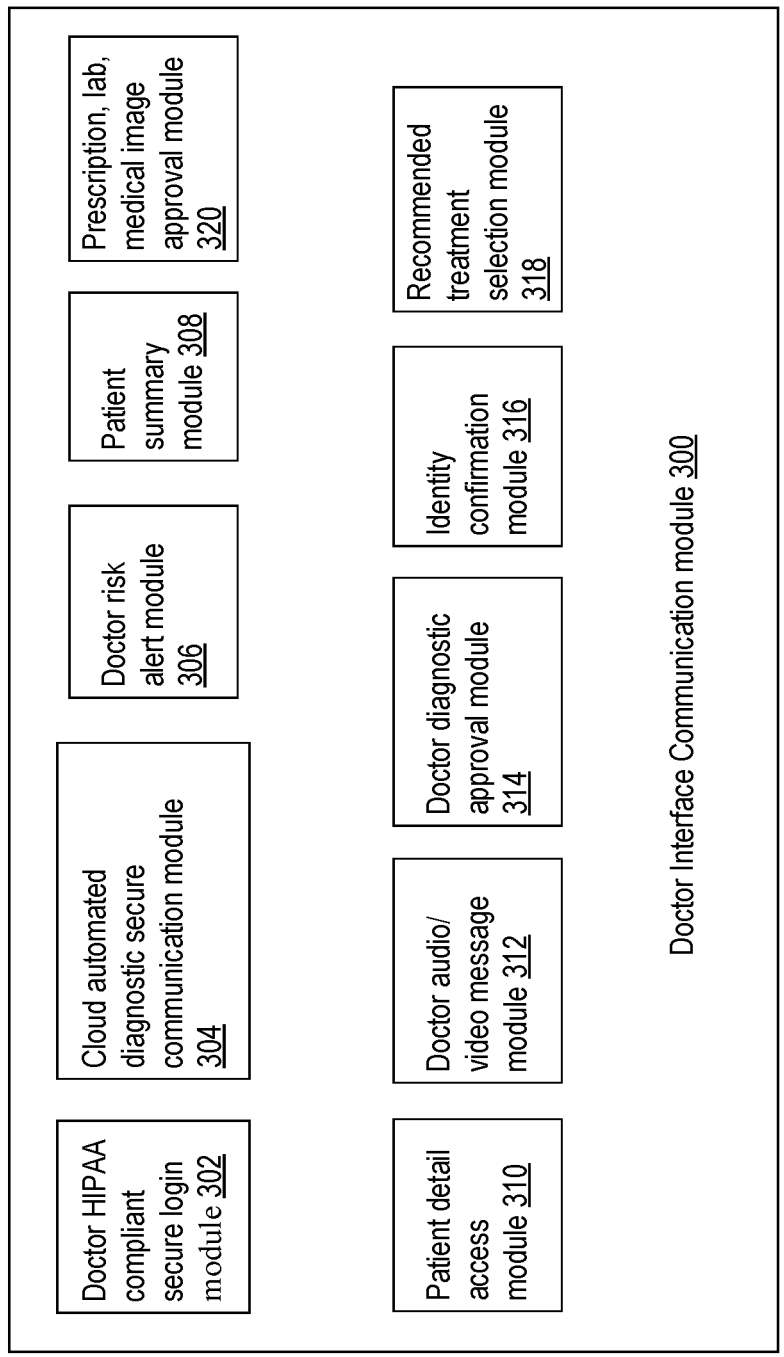
FIG. 3 shows a schematic diagram of a doctor interface communication module according to embodiments of the present disclosure.

FIG. 3 shows a schematic diagram of a doctor interface communication module according to embodiments of the present disclosure. In embodiments, doctor interface communication module 300 (or 130 in FIG. 1) may be installed in doctor interface station 104 (shown in FIG. 1). In embodiments, each component of the doctor interface communication module 300 in FIG. 3 may be implemented as software, hardware, and/or firmware. It is noted that components 302-314 are not exhaustive list of elements that may comprise doctor interface communication module 300. Also, it is noted that some of components 302-314 may be combined into one element and one component may be implemented as multiple elements.

In embodiments, doctor interface communication module 300 comprises: doctor HIPAA compliant secure login module 302 that may maintain an automated diagnostic system (not shown in FIG. 3) compliant with HIPAA regulations and allow a physician with access privileges to log into the automated diagnostic system, for example, via identity confirmation module 316; cloud automated diagnostic secure communication module 304 that may provide secure communication between a cloud system and the physician; doctor risk alert module 306 that may provide a risk profile of the patient to the physician to assist the physician in reviewing and referring for further testing or providing an alert or notice to the physician when the risk profile is above a certain threshold or when the application determines that the patient has multiple illness or a patient malpractice risk score is above a certain threshold; patient summary module 308 that may provide a patient status and diagnosis overview; patient detail access module 310 that may provide detailed information about the patient to a physician for review; doctor audio/video message module 312 that may transmit to or receive from the physician various audio/video messages; doctor optional diagnostic approval module 314 that may allow the physician to approve a diagnostic output from the automated diagnostic system; and prescription, lab, medical image approval module 320 that may allow the physician to approve tests and imaging procedures; and recommended treatment selection module 318 that may allow the physician to select a recommended treatment.

Figure 4:
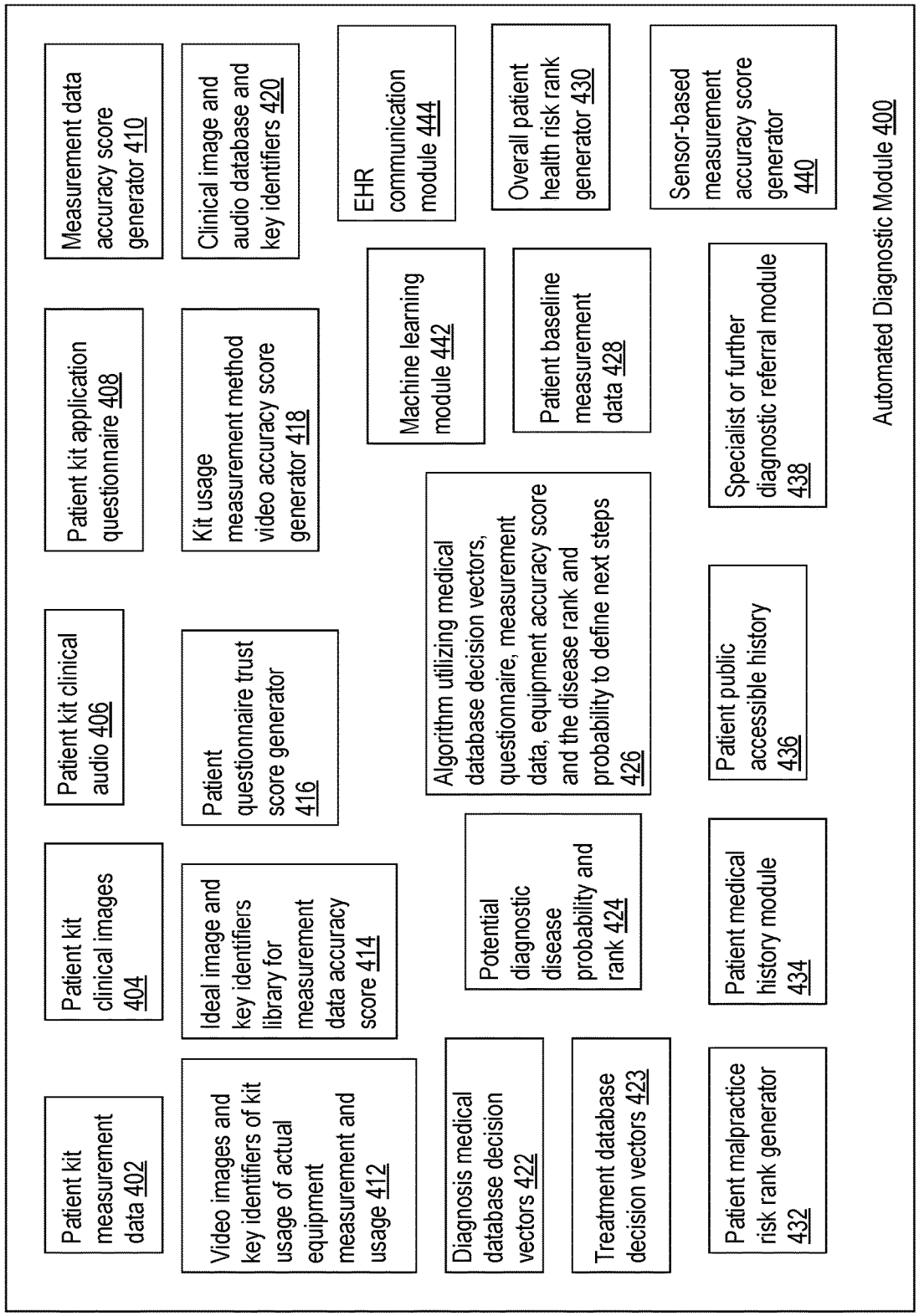
FIG. 4 shows a schematic diagram of an automated diagnostic module according to embodiments of the present disclosure.

FIG. 4 shows a schematic diagram of an automated diagnostic module according to embodiments of the present disclosure. In embodiments, automated diagnostic module 400 may be installed in the automated diagnostic system (not shown in FIG. 4). In embodiments, each component of automated diagnostic module 400 may be implemented as software, hardware, and/or firmware. It is noted that components 402-438 are not exhaustive list of elements that comprise the automated diagnostic module 400. Also, it is noted that some of the components 402-438 may be combined into one element and one component may be implemented as multiple elements.

In embodiments, automated diagnostic module 400 comprises: patient kit measurement data 402 that may be a repository for the measurement data delivered from the patient kit and/or the patient; patent kit clinical images 404 that may be a repository for images related to the patient diagnosis condition being evaluated; patient kit clinical audio 406 that may be a repository for auditory files related to the patient diagnosis condition being evaluated; and patent kit application questionnaire 408 that may be a repository for a question-answer history.

In embodiments, automated diagnostic module 400 comprises software 410-418 that may determine the accuracy, reliability, and a trust score for measurement data, images, audio files and data in a questionnaire. In embodiments, automated diagnostic module 400 comprises measurement data accuracy score generator 410 that may calculate the measurement accuracy score and data accuracy score of measured raw data. Measurement reliability and accuracy score may be determined based on an accuracy of a medical device usage, for example, by comparing images of the patient taking data to sample ideal images to determine whether instructions were properly followed.

In embodiments, measurements may be monitored by a camera and compared against ideal measurement images to assure accurate placement. In embodiments, measurement data accuracy score generator 410 analyzes the data for accuracy, e.g., by comparing to actual measurement data to sample or historical model data to provide a data accuracy score for the actual measurement data.

In embodiments, automated diagnostic module 400 may comprise: video images and key identifiers of kit image of actual equipment measurement and usage 412 and ideal image and key identifiers library for measurement data accuracy score 414, where the images, video, sensor data stored in the two components 412 and 414 are used by measurement data accuracy score generator 410 to determine the kit usage measurement method sensor accuracy. In embodiments, measurement data accuracy score generator 410 generates a score for one or more medical devices in the kit, e.g., by observing the actual measured data and comparing it to an acceptable threshold of measurement data.

In embodiments, automated diagnostic module 400 comprises patient questionnaire trust score generator 416 that may assign a score to a patient's responses to questions in a questionnaire, for example, based on the speed of answering, patient history, probability of a specific question being erroneous, patient-related public information, answers to other related questions, and relative accuracy of other patients' answers to a specific question.

In embodiments, automated diagnostic module 400 comprises: kit usage measurement method video accuracy score generator 418 that may determine the accuracy and reliability of the use of measurement equipment as monitored by video; sensor-based measurement accuracy score generator 440 may specifically create a measurement accuracy score for each of one or more sensors in the kit; a clinical image and audio database and key identifiers 420 that may comprise data of clinical diseases and their traits, where the data relates to images and audio analysis to be used as a match library for patient submitted images.

In embodiments, automated diagnostic module 400 comprises: medical database decision vectors 422 that may determine the likelihood of a potential disease based on generally accepted general practitioner guidelines incorporating potential diagnoses for diseases, patient inputs, measurement data, history, patient baseline data, and other data. In embodiments, automated diagnostic module 400 comprises a database that receives updates from machine learning module 442 utilizing the patient and doctor data during usage and recent medical research findings and historical medical records. In embodiments, medical database decision vectors 422 may be used to output a list of potential disease, e.g., with suggestions for additional steps for decreasing the number of potential diseases. In embodiments, treatment database decision vectors 423 may be used to output a list of potential treatments.

In embodiments, automated diagnostic module 400 comprises: potential diagnostic disease probability and rank 424 that may be a repository for the output decision vector 422 and include a list of potential diseases and the probability of each disease based on patient input, accuracy rank of questionnaire, measurement method, and measurement data.

In embodiments, automated diagnostic module 400 comprises: algorithm 426 that may utilize output medical database decision vector 422, questionnaire, measurement data, equipment accuracy score, and a disease rank/probability to recommend additional steps; machine learning module 442 for diagnostic/treatment database and medical equipment usage; patient baseline measurement data 428 may be obtained using the diagnostic kit when the patient is in a relatively healthy condition; overall patient health risk rank generator 430 that may generate the rank of the overall patient heath risk; overall patient malpractice risk rank generator 432 that may generate a malpractice risk score; patient medical history module 434 that may maintain the medical history of the patient and key identifiers that may be used by a diagnostic algorithm; patient public accessible history 436 that may be a tool for accessing, recovering, and storing publically available patient data, such as civil and criminal court data, malpractice involvement, press activity, social profile and activity; specialist or further diagnostic referral module 438 that may provide information regarding a specialist or a diagnostic referral for further testing or treatment; and EHR communication module 444 to retrieve and update patient health records.

Figure 5:
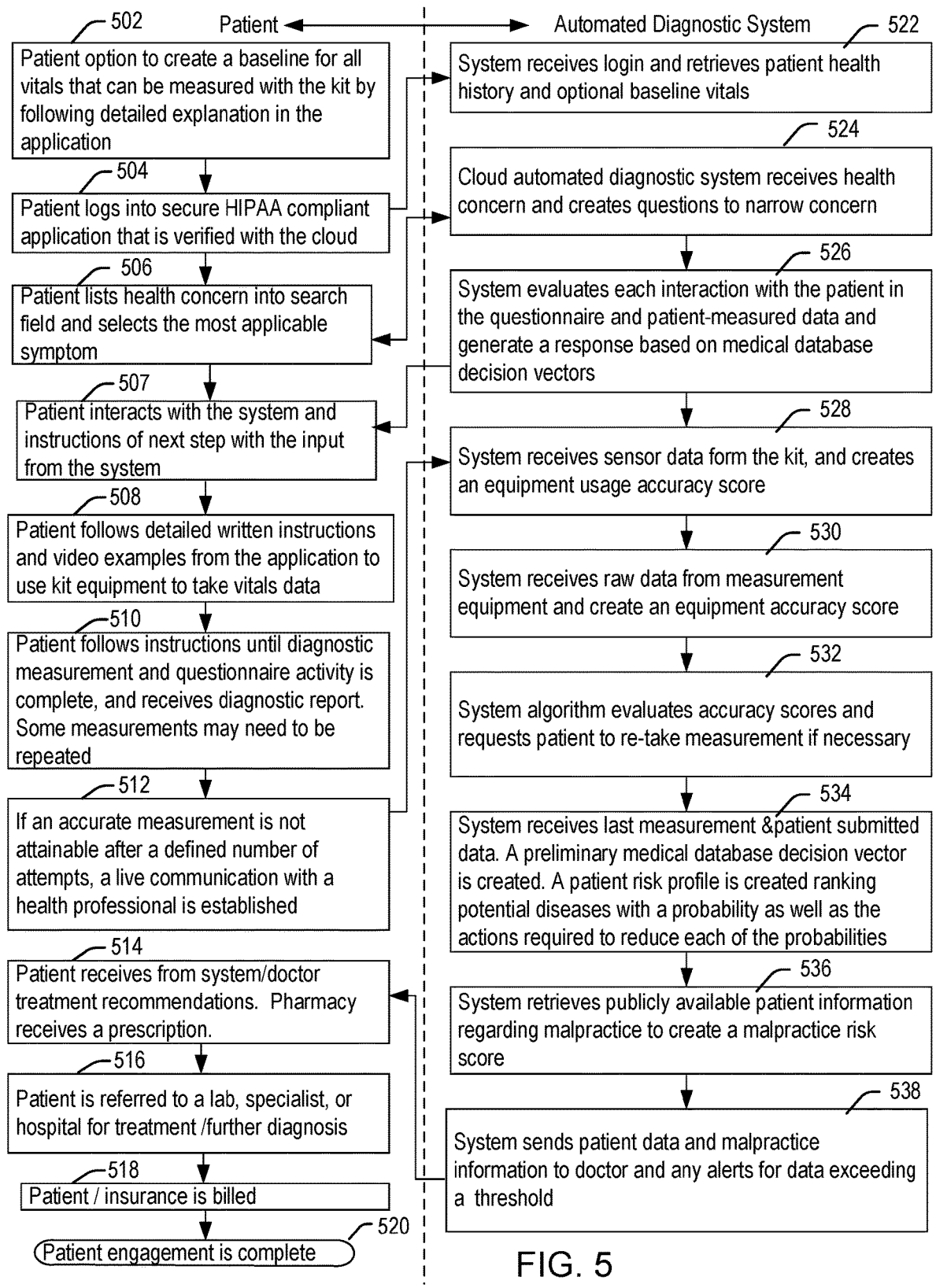
FIG. 5 shows a flowchart of an illustrative process for providing medical consulting services, according to embodiments of the present disclosure.

FIG. 5 shows a flowchart of an illustrative process for providing medical consulting services, according to embodiments of the present disclosure. In embodiments, process 500 allows patients to use diagnostic equipment, e.g., in a kit at a kiosk comprising a display, to self-measure vital signs with a certain degree of accuracy by following instructions. In embodiments, a kiosk comprising an automated diagnostic system may provide instructions and detailed explanations and an option to create a baseline for vital signs.

At step 504, the patient may log into an application, e.g., a secure HIPAA compliant application, that is verified via a network.

At step 522, the automated diagnostic system may be used to retrieve patient-related data, such as health history and baseline vital signs.

At step 506, the patient may enter health concerns into a search field and select the most applicable symptom form a list of options.

At step 524, the automated diagnostic system may receive the entries and create questions to narrow down the concerns.

At step 526, the automated diagnostic system may evaluate each interaction with the patient in the questionnaire and patient-measured data to generate response, e.g., based on medical database decision vectors. At this point, process 500 may continue with step 507 where the patient may interact with the system and receive instructions of next step with the input from step 526.

At step 508, the patient may follow detailed written instructions and video examples provided by the application to use diagnostic equipment to take vital signs data.

At step 510, the patient may follow instructions until diagnostic measurement and questionnaire activity is complete, and receive a diagnostic report. Some measurements may need to be repeated.

At step 512, if an accurate measurement is not attainable after a defined number of attempts, a live communication with a health professional, e.g., through video and/or audio or in person, may be established.

At step 528, the automated diagnostic system may use camera, location proximity sensors, accelerometers, gyro, pressure sensor, altimeter, and other sensors of the kit and create an equipment usage accuracy score therefrom.

At step 530, the automated diagnostic system may receive raw data from measurement equipment and create an accuracy score representative of the accuracy of the diagnostic equipment used by the patient.

At step 532, the accuracy scores may be evaluated and, if they fall below a predetermined threshold, the patient may be requested to repeat a measurement. In embodiments, for each individual device, the threshold may be adjusted, e.g., by using machine learning process.

At step 534, the automated diagnostic system may comprise a preliminary medical database decision vector and a patient risk profile may be created, ranking potential diseases by probability as well as the actions required to further refine a diagnosis.

At step 536, the automated diagnostic system may retrieve publicly available patient information related to malpractice cases to generate a malpractice risk score.

At step 538, the automated diagnostic system may send patient data and malpractice information to a doctor and any alerts for data that exceeds a predetermined threshold that may be adjusted for each patient, e.g., by using a machine learning process.

At step 514, the patient may receive treatment recommendation through the system or from the medical professional. The treatment may include prescription delivery information, and the patient's pharmacy may receive a prescription directly from the system.

At step 516, the patient may be referred to a specialist, a lab, or a hospital for treatment or other location for further diagnosis.

At step 518, the patient and/or the patient's insurance and/or the patient may be billed.

At step 520, the patient engagement may be completed.

Figure 7:
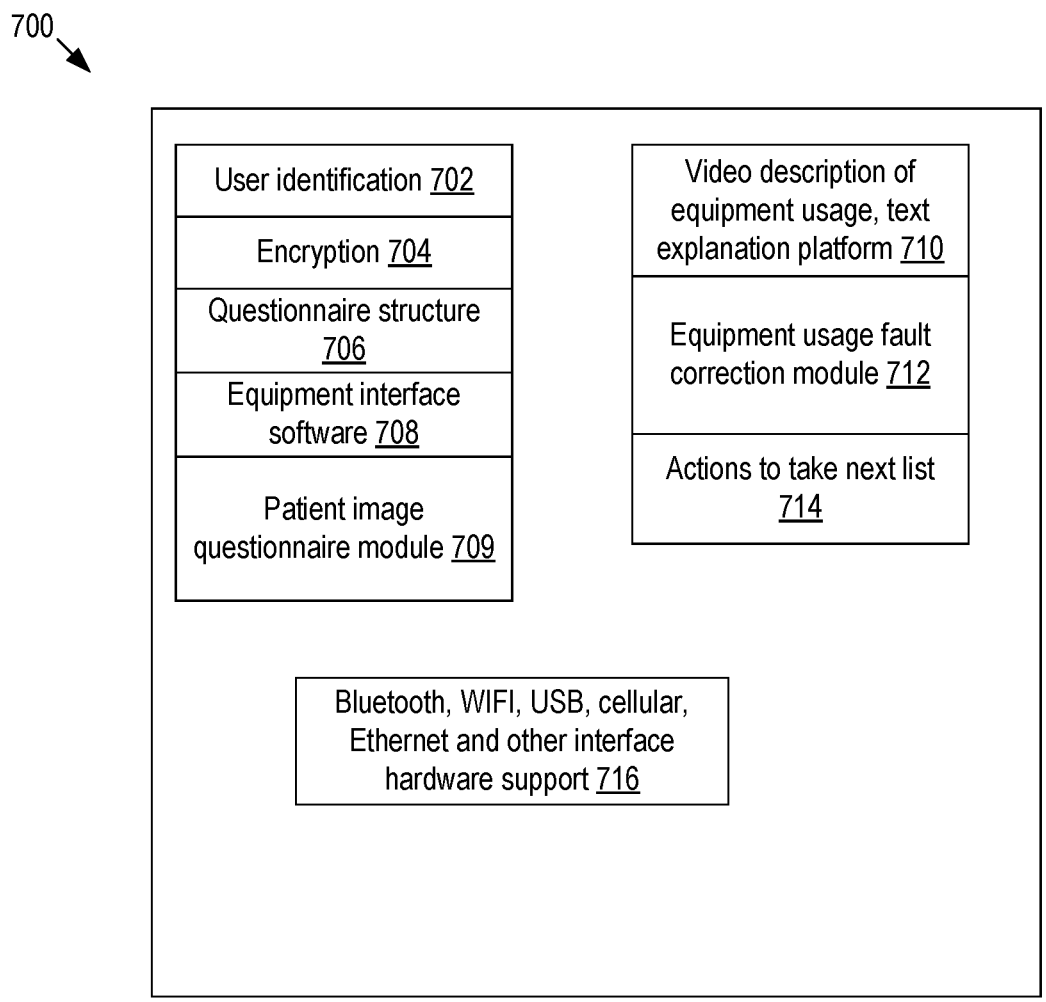
FIG. 7 shows a schematic block diagram of a patient application interface according to embodiments of the present disclosure.

FIG. 7 shows a schematic block diagram of a patient application interface according to embodiments of the present disclosure. In embodiments, application interface 700 may be installed in patient interface station 106 (shown in FIG. 1) and comprise hardware, software, and/or firmware components that establish an interaction with a patient.

In embodiments, application interface 700 comprises user identification 702, which may comprise a login system that may use biometric data, a keyboard entry, or any other suitable device to authenticate a patient; encryption 704 that may support HIPAA compliant transmission; questionnaire structure 706 that may receive questions and answers from a cloud-based system that are tailored to each patient based on the patient's entries; equipment interface software 708 that may be middleware for communicating with and receiving data from the diagnostic equipment; patient image questionnaire module 709 that may display an image to aid a patient in describing body location having symptoms; video description of equipment usage and text explanation platform 710 that may include a video and text display and a storage support framework for enabling video and text playback and control; equipment usage fault correction module 712 that may, upon detecting a usage error, provide instructions to a patient in correctly using and taking measurements on diagnostic equipment; a list of actions to take next 714 that may display explanatory alerts (e.g., that a doctor is coming) in an urgent care setting, treatments, or patient instructions requesting/suggesting further tests as a next step; and interface hardware support 716, such as Bluetooth, WIFI, USB, cellular, Ethernet, and other interface hardware support, that may include communication hardware, firmware, and driver framework to facilitate operation of one or more modules.

In embodiments, one or more computing systems, such as mobile/tablet/computer or the automated diagnostic system, may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present disclosure may be implemented in any instruction-execution/computing device or system capable of processing data, including, without limitation phones, laptop computers, desktop computers, and servers. The present disclosure may also be implemented into other computing devices and systems. Furthermore, aspects of the present disclosure may be implemented in a wide variety of ways including software (including firmware), hardware, or combinations thereof. For example, the functions to practice various aspects of the present disclosure may be performed by components that are implemented in a wide variety of ways including discrete logic components, one or more application specific integrated circuits (ASICs), and/or program-controlled processors. It shall be noted that the manner in which these items are implemented is not critical to the present disclosure.

Figure 13:
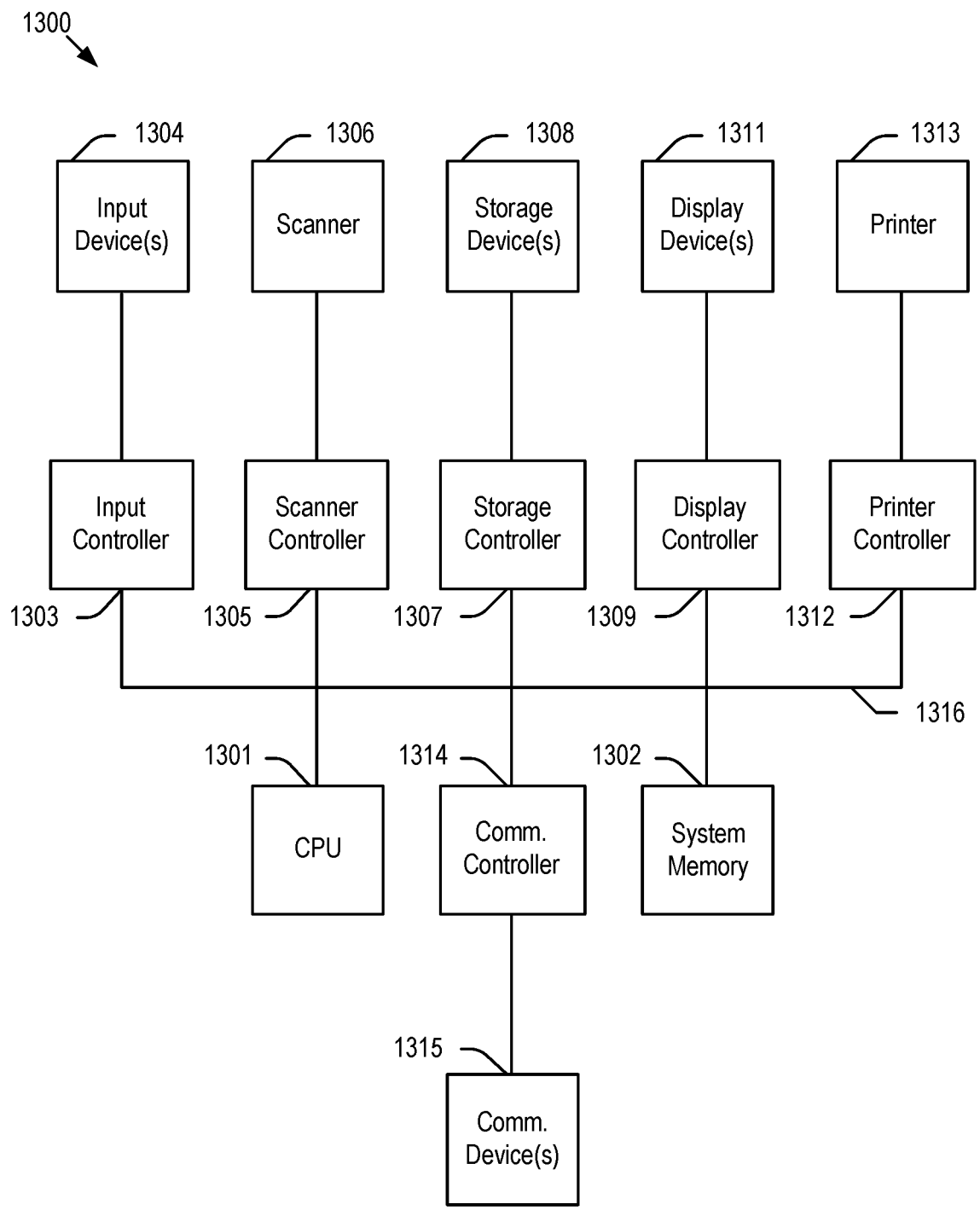
FIG. 13 depicts a computer system to according to embodiments of the present disclosure.

Having described the details of the disclosure, an exemplary system 1300, which may be used to implement one or more aspects of the present disclosure, will now be described with reference to FIG. 13. Each of patient interface station 106 and automated diagnostic system 102 in FIG. 1 may comprise one or more components in the system 1300. As illustrated in FIG. 13, system 1300 includes a central processing unit (CPU) 1301 that provides computing resources and controls the computer. CPU 1301 may be implemented with a microprocessor or the like, and may also include a graphics processor and/or a floating point coprocessor for mathematical computations. System 1300 may also include a system memory 1302, which may be in the form of random-access memory (RAM) and read-only memory (ROM).

A number of controllers and peripheral devices may also be provided, as shown in FIG. 13. An input controller 1303 represents an interface to various input device(s) 1304, such as a keyboard, mouse, or stylus. There may also be a scanner controller 1305, which communicates with a scanner 1306. System 1300 may also include a storage controller 1307 for interfacing with one or more storage devices 1308 each of which includes a storage medium such as magnetic tape or disk, or an optical medium that might be used to record programs of instructions for operating systems, utilities and applications which may include embodiments of programs that implement various aspects of the present disclosure. Storage device(s) 1308 may also be used to store processed data or data to be processed in accordance with the disclosure. System 1300 may also include a display controller 1309 for providing an interface to a display device 1311, which may be a cathode ray tube (CRT), a thin film transistor (TFT) display, or other type of display. System 1300 may also include a printer controller 1312 for communicating with a printer 1313. A communications controller 1314 may interface with one or more communication devices 1315, which enables system 1300 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 1316, which may represent more than one physical bus. However, various system components may or may not be in physical proximity to one another. For example, input data and/or output data may be remotely transmitted from one physical location to another. In addition, programs that implement various aspects of this disclosure may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present disclosure may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter.

Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

For purposes of this disclosure, an information handling system may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an information handling system may be a personal computer (e.g., desktop or laptop), tablet computer, mobile device (e.g., personal digital assistant (PDA) or smart phone), server (e.g., blade server or rack server), a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, touchscreen and/or a video display. The information handling system may also include one or more buses operable to transmit communications between the various hardware components.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure.

I claim:

1. An apparatus for self-diagnosis of a medical condition, the apparatus comprising:
    at least one medical instrument comprising a medical sensor and an identifiable marker, the at least one medical instrument configured to be positioned at a preferred location relative to a user body, the at least one medical instrument being tracked relative to the preferred location using location information generated from the identifiable marker to enable a display of a first position of the at least one medical instrument relative to the user body and to guide the user in positioning the at least one medical instrument closer to the preferred location;
    a camera coupled to track the identifiable marker and to generate the location information of the at least one medical instrument relative to the preferred location;
    a location processing element coupled to receive the location information from the camera, the location processing element determines a position accuracy measurement of the first location of the at least one medical instrument relative to the preferred location on the user body and generates a response indicative of the position accuracy measurement;

a location verification element coupled to receive the response, the location verification element determines whether the position accuracy measurement is within a predefined numerical range, if the position accuracy measurement is outside of the predefined numerical range then providing feedback on the display to the user to adjust the first location of the at least one medical instrument to a second location that is closer to the preferred location;

a diagnosis processing element coupled to receive patient measurement data from the at least one medical instrument if the position accuracy measurement is within the predefined numerical range, the diagnosis processing element associates the patient measurement data with at least one medical diagnosis; and a verification processing element coupled to receive the patient measurement data and the at least one medical diagnosis, the verification processing element generates a diagnostic rating value that identifies a confidence value of the at least one medical diagnosis based at least partially on the position accuracy measurement, the patient measurement data, or the at least one medical diagnosis.

2. The apparatus according to claim 1, wherein the identifiable marker is an IR LED.

3. The apparatus according to claim 2, further comprising a camera that uses the reference data to identify the preferred location.

4. The apparatus according to claim 1, wherein the diagnostic rating value is representative of an accuracy of the at least one medical instrument.

5. The apparatus according to claim 1, wherein the diagnosis processing element assigns a diagnosis probability to potential illness based on one or more weight factors.

6. The apparatus according to claim 1, wherein the at least one sensor comprises at least one of an accelerometer, a gyroscope, or a magnetometer.

7. A system for self-diagnosis of a medical condition, the system comprising:
  a patient interface coupled to receive patient data;
  a medical instrument coupled to the patient interface, the medical instrument configured to be positioned at a target position relative to a user body to generate patient measurement data, the medical instrument comprising an identifiable marker that guides the user in positioning the at least one medical instrument closer to the target position;
  a sensor coupled to the medical instrument, the sensor configured to generate position information relative to a first position of the medical instrument;
  a position processor coupled to receive the first position information to determine a position accuracy measurement that relates the first position to the target position and generates a response indicative of the position accuracy measurement;
  a comparator coupled to the position processor, the comparator determines whether the position accuracy measurement is within a predefined numerical range;
  a verification processor coupled to the comparator, the verification processor generates an accuracy score based on at least one of the position accuracy measurement and the patient measurement data; and
  a diagnosis processor coupled receive the patient measurement data from to the medical instrument and at least one accuracy score from the verification processor to generate at least one medical diagnosis.

8. The system according to claim 7, further comprising a doctor interface coupled to the verification processor, the doctor interface receives the accuracy score from the verification processor.

9. The system according to claim 8, wherein the at least one medical diagnosis is used to output medical information to at least one of the patient interface and the doctor interface.

10. The system according to claim 7, wherein the diagnosis processor assigns diagnosis probabilities to potential illness based on one or more weight factors.

11. The system according to claim 10, wherein the diagnosis processor eliminates one or more of the potential illnesses based on one or more diagnosis probabilities.

12. A method for self-diagnosis of a medical condition, the method comprising:
  in response to a medical instrument being positioned at a preferred location relative to a user body, receiving patient measurement data and position information relative to a first position of the medical instrument, the medical instrument comprising a medical sensor and an identifiable marker, the identifiable marker guides a user in positioning the at least one medical instrument closer to the preferred location;
  based on the first position information, determining a position accuracy measurement to relate the first position to the preferred position and generate a response indicative of the position accuracy measurement;
  in response to determining that the position accuracy measurement being within a predefined numerical range, associating the patient measurement data with at least one medical diagnosis, if the position accuracy measurement is outside of the predefined numerical range then providing feedback to the user to adjust the location of the at least one medical instrument closer to the preferred location; and
  generating a diagnostic rating value based on at least one of the position accuracy measurement, the patient measurement data, or the at least one medical diagnosis.

13. The method according to claim 12, wherein further comprising assigning diagnosis probabilities to potential illness based on one or more weight factors.

14. The method according to claim 12, further comprising comparing the at least one medical diagnosis with one or more diagnoses in a treatment database to generate treatment information.

15. The method according to claim 14, further comprising automatically populating an electronic health record with at least one of a diagnosis code or a treatment code in response receiving at least one of the patient measurement data or the patient input data.

* * * * *